United States Patent
Garcia et al.

(10) Patent No.: US 8,114,431 B2
(45) Date of Patent: Feb. 14, 2012

(54) BIOMOLECULAR COATING FOR IMPLANTS

(75) Inventors: Andres J. Garcia, Atlanta, GA (US); Catherine D. Reyes, Miami, FL (US); Timothy Petrie, Atlanta, GA (US); Zvi Schwartz, Atlanta, GA (US); Barbara D. Boyan, Atlanta, GA (US); Jenny E. Raynor, E. Sandwich, MA (US); David M. Collard, Atlanta, GA (US); Abigail M. Wojtowicz, Atlanta, GA (US); Robert E. Guldberg, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1044 days.

(21) Appl. No.: 11/857,819

(22) Filed: Sep. 19, 2007

(65) Prior Publication Data

US 2008/0131425 A1 Jun. 5, 2008

Related U.S. Application Data

(60) Provisional application No. 60/826,193, filed on Sep. 19, 2006.

(51) Int. Cl.
*A61F 2/00* (2006.01)
*A61K 38/00* (2006.01)
*A61K 51/00* (2006.01)
*C07K 2/00* (2006.01)
*C07K 4/00* (2006.01)
*C07K 5/00* (2006.01)
*C07K 7/00* (2006.01)
*C07K 9/00* (2006.01)
*C07K 16/00* (2006.01)
*C07K 17/00* (2006.01)

(52) U.S. Cl. ......... 424/423; 530/300; 424/1.69; 514/1.1
(58) Field of Classification Search .................. None
See application file for complete search history.

(56) References Cited

U.S. PATENT DOCUMENTS 5,302,701 A * 4/1994 Hashi et al. .................. 530/399

OTHER PUBLICATIONS

Coussen et al. Trimers of the fibronectin cell adhesion domain localize to actin filament bundles and undergo rearward translocation. (J Cell Sci. Jun. 15, 2002;115(Pt 12):2581-90).*
Anderson "Biological responses to Materials" *Annu Rev Mater Res* 31:81-110(2001).
Barber "Peri-implant bone formation and implant integration strength of peptide-modified p(AAM-co-EG/AAC) interpenetrating polymer network-coated titanium implants," *J Biomed Mater Res A* 80:306-320(2007).
Baron, "1H NMR Assignment and Secondary Structure of the Cell Adhesion Type III Module of Fibronectin," *Biochemistry* 31(7): 2068-2073(1992).
Baron, "Structure of the Fibronectin Type I Module," *Nature*. 345: 642-646 (1990).

(Continued)

*Primary Examiner* — Maury Audet
(74) *Attorney, Agent, or Firm* — Pabst Patent Group LLP

(57) ABSTRACT

Methods and compositions are provided for improving tissue growth and device integration in vivo. Substrates and devices coated with an $\alpha_2\beta_1$ or $\alpha_5\beta_1$ integrin-specific ligand are provided. The substrates and devices coated with an $\alpha_2\beta_1$ or $\alpha_5\beta_1$ integrin-specific ligand are shown to have greater tissue formation on the surface relative to controls, in particular greater bone formation.

11 Claims, 21 Drawing Sheets

OTHER PUBLICATIONS

Bauer, "The pathology of total joint arthroplasty. I. Mechanisms of implant fixation," *J Skeletal Radiol* 28:423-432(1999).

Bauer, "The pathology of total joint arthroplasty.II. Mechanisms of implant failure," *Skeletal Radiol* 28:483-497(1999).

Cutler and Garcia, "Engineering cell adhesive surfaces that direct intergin alpha5beta1 binding using a recombinant fragment of fibronectin," *Biomaterials*, 24:1759-70 (2003).

Ducy, "Osf2/Cbfa1: a transcriptional activator of osteoblast differentiation," *Cell* 89:747-754(1997).

Elmengaard "In vivo study of the effect of RGD treatment on bone ongrowth on press-fit titanium alloy implants" *Biomaterials* 26:3521-3526(2005).

Ffrench-Constant, "Alternative Splicing of Fibronectin—Many Different Proteins but Few Different Functions," *Exp. Cell. Res.* 221: 261-271(1995).

Gallant, "Cell adhesion strengthening: contributions of adhesive area, integrin binding, and focal adhesion assembly," *Mol. Biol. Cell* 16:4329-4340(2005).

Garcia, "Get a grip: integrins in cell-biomaterial interactions," *Biomaterials* 26:7525-7529(2005).

Hanks, "Focal adhesion kinase signaling activities and their implications in the control of cell survival and motility," *Front Biosci* 8:d982-d996 (2003).

Hubbell, "Biomaterials science and high-throughput screening," *Nat Biotechnol* 22:828-829(2004).

Hynes, "Integrins: bidirectional, allosteric signaling machines," *Cell* 110:673-687(2002).

Keselowsky "Integrin binding specificity regulates biomaterial surface chemistry effects on cell differentiation," *Proc Natl Acad Sci U S A* 102:5953-5957 (2005).

Keselowsky, "Quantitative methods for analysis of integrin binding and focal adhesion formation on biomaterial surfaces," *Biomaterials* 26:413-418 (2005).

Langer, "Designing materials for biology and medicine," *Nature* 428:487-492 (2004).

Lutolf, "Synthetic biomaterials as instructive extracellular microenvironments for morphogenesis in tissue engineering," *Nat Biotechnol* 23:47-55(2005).

Main, et al. "The Three-Dimensional Structure of the Tenth Type III Module of Fibronectin: An Insight into RGD-Mediated Interactions," *Cell* 71: 671-678(1992).

Petrie, "Integrin specificity and enhanced cellular activities associated with surfaces presenting a recombinant fibronectin fragment compared to RGD supports," *Biomaterials* 27:5459-5470(2006).

Pilliar, "Cementless implant fixation—toward improved reliability," *Orthop Clin North Am* 36:113-119 (2005).

Potts, "Fibronectin Structure and Assembly," *Curr. Cell Bio.* 6:648-655(1994).

Potts, "Structure and Function of Fibronectin Modules," *Matrix Bio.* 15: 313-320(1996).

Raynor "Controlling Cell Adhesion to Titanium: Functionalization of Poly[oligo(ethylene glycol)methacrylate] Brushes with Cell-Adhesive Peptides," *Adv Mater.* 19(13):1724-1728 (2007).

Reyes, "A centrifugation cell adhesion assay for high-throughput screening of biomaterial surfaces," *J Biomed Mater Res* 67A:328-333(2003).

Reyes,"Biomolecular surface coating to enhance orthopaedic tissue healing and integration," *Biomaterials* 28(21):3228-35 (2007).

Schliephake "Effect of RGD peptide coating of titanium implants on periimplant bone formation in the alveolar crest. An experimental pilot study in dogs," *Clin. Oral Implants Res.* 13:312-319(2002).

Tamura, "Focal adhesion kinase activity is required for bone morphogenetic protein—Smad1 signaling and osteoblastic differentiation in murine MC3T3-E1 cells," *J. Bone Miner. Res.* 16:1772-1779(2001).

* cited by examiner

BIOMOLECULAR COATING FOR IMPLANTS

CROSS REFERENCE TO RELATED APPLICATIONS

This application claims priority to and benefit of U.S. Provisional Application No. 60/826,193 filed Sep. 19, 2006, and where permissible is incorporated herein in its entirety.

STATEMENT REGARDING FEDERALLY SPONSORED RESEARCH OR DEVELOPMENT

Aspects of the work described herein were supported by Grant No, R01 EB-004496 awarded by the National Institutes of Health, Grant No. DTD 000207 awarded by the Arthritis Foundation, and Grant No. ERC EEC-9731643 awarded by the National Science Foundation. Therefore the U.S. government has certain rights in the claimed subject matter.

REFERENCE TO SEQUENCE LISTING

The Sequence Listing submitted Sep. 1, 2011 as a text file named "GTRC_3967_ST25.txt," created on Aug. 25, 2011, and having a size of 6,318 bytes is hereby incorporated by reference pursuant to 37 C.F.R. §1.52(e)(5).

TECHNICAL FIELD

This disclosure is generally directed to biomolecular coatings for biomedical devices and implants and methods for improving device integration into tissues and methods for treating tissue defects or diseases including, but not limited to bone defects, disorders, or diseases.

BACKGROUND

Upon implantation, synthetic materials elicit an inflammatory response that results in a foreign body reaction and fibrous encapsulation. The foreign body reaction severely limits device integration and in viva performance of numerous biomedical devices, including chemical biosensors, electrical leads/electrodes, therapeutic delivery systems, and orthopaedic and cardiovascular prostheses. Extensive efforts have concentrated on surface treatments and coatings to improve host tissue-implant integration. For instance, current orthopaedic and dental implant surface technologies focus on rough/porous coatings for bone ingrowth and bone-bonding ceramic coatings to promote integration with the surrounding bone. However, while these approaches are generally successful, they can be restricted by slow rates of osseointegration and poor mechanical anchorage in challenging clinical cases, such as those associated with large bone loss and poor bone quality. Since the extracellular matrix controls cell adhesion and function, recent biomimetic strategies have focused on the immobilization of matrix components, including native proteins, peptide sequences, or synthetic derivatives based on matrix molecules. Full-length extracellular matrix proteins are attractive biomimetic targets for functionalizing orthopaedic implant surfaces in order to promote healing, bone formation, and implant fixation. However, these full-length protein strategies are limited by lack of specificity for particular cellular receptors and downstream signaling events and thus allow minimal control over cell and tissue responses. In addition, native ECM proteins often have binding sites for other ligands, such as fibrinogen or von Willebrand factor. Such ligands trigger separate signaling cascades that may ultimately confound phenotypic responses and interfere with controlled cell function.

The most common peptide-based strategy involves the surface deposition of peptides containing the Arg-Gly-Asp (RGD) sequence, which mediates cell attachment to several matrix proteins, including fibronectin, vitronectin, osteopontin, and bone sialoprotein. However, these bio-inspired strategies have yielded marginal increases in implant integration and mechanical fixation. Because RGD is recognized by a large number of integrins in numerous cell types, this approach lacks specificity for particular targeted integrin signaling events and results in non-discriminatory attachment of cells to the RGD-coated surfaces.

Therefore, it is an object of the invention to provide methods and compositions to improve implant integration in vivo.

It is still another object to provide devices and implants coated with biomolecular compositions for increasing tissue integration of the device.

It is yet another object to provide methods and compositions for treating bone defects, bone disorders, or diseases of the bone.

SUMMARY

Methods and compositions are provided for improving device integration into tissue, treating tissue disorders and defects such as bone defects, bone disorders, or diseases of the bone. One aspect provides methods and compositions for improving implant integration into tissue. The tissue can be osseous, cardiovascular, skin, liver or kidney tissue. One aspect provides methods and compositions for improving tissue growth on or in an implant, or a combination thereof. Another aspect provides a device, for example an implant having an integrin-specific ligand in an amount effective to promote tissue growth, implant integration, or a combination thereof in vivo. Another aspect provides a device, for example an orthopaedic, dental, cardiovascular, liver, or kidney device having an $\alpha_2\beta_1$ integrin ligand, an $\alpha_5\beta_1$ integrin ligand, or a combination thereof coated on a surface of the device. Representative $\alpha_2\beta_1$ integrin ligands include, but are not limited to, a peptide having at least 80% sequence identity to GGYGGGPC(GPP)$_5$GFOGER(GPP)$_5$GPC (SEQ ID NO:1, referred to herein as "GFOGER peptide"). Representative $\alpha_5\beta_1$ integrin ligands include, but are not limited to FNIII$_{7-10}$. In certain aspects, the integrin ligand is applied to the surface of the device in an amount effective to promote tissue formation, device integration, or both in vivo relative to a control. A control includes a similar device without the integrin ligand.

Another aspect provides a method for improving implant integration by coating the surface of the implant with an $\alpha_2\beta_1$ integrin ligand, an $\alpha_5\beta_1$ integrin ligand, or a combination thereof. The integrin ligand can be passively adsorbed to the surface of the implant. Typically, the implant is made of metal such as clinical grade titanium (Ti) or a polymer, for example polycaprolactone. In other embodiments, the integrin ligand is coupled to the surface of the device by a linker. A representative linker includes, but is not limited to, self-assembled monolayers (SAMs) of alkanethiols.

DETAILED DESCRIPTION

I. Compositions

Figure 1:
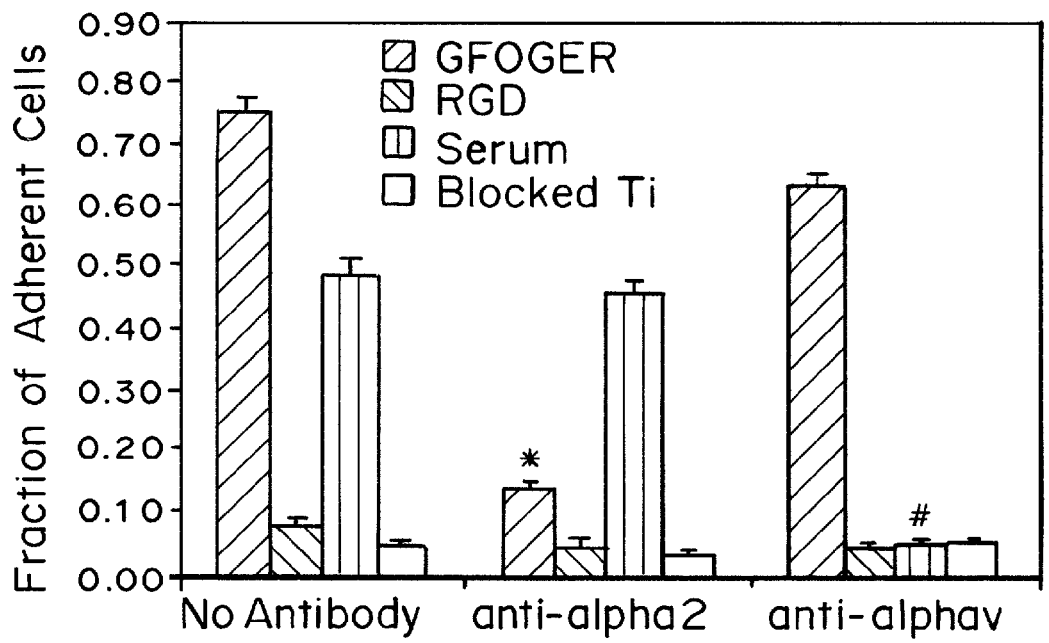
FIG. 1 is a bar graph showing the fraction of adherent cells on Ti surfaces adsorbed with "GFOGER peptide" (GGYGGGPC(GPP)$_5$GFOGER(GPP)$_5$GPC, SEQ ID NO:1), adsorbed with linear "RGD peptide" (GRGDSPC, SEQ ID NO:3), adsorbed fetal bovine serum (10% in PBS), and non-adhesive blocked Ti in the presence or absence of blocking antibodies against alpha2 or alphaV integrin subunit.

One embodiment provides a substrate or device, for example an orthopaedic or dental device, such as an implant, coated with a ligand for $\alpha_2\beta_1$ integrin, a ligand of $\alpha_5\beta_1$ integrin, or a combination thereof. In certain embodiments the ligand interacts specifically with one integrin. In still other embodiments, the ligand is not a complete fibronectin molecule or is not a complete collagen molecule.

A. Integrin Ligands

The $\alpha_2\beta_1$ integrin is highly expressed on osteoblasts and other mesenchymal cells and is one of the predominant adhesion receptors for type I collagen. $\alpha_2\beta_1$ integrin-type I collagen interactions provide crucial signals for the induction of osteoblastic differentiation and matrix mineralization. For example, $\alpha_2\beta_1$-mediated osteoblast adhesion to type I collagen activates Runx2/Cbfa1, a transcription factor that regulates osteogenesis. Furthermore, the collagen-$\alpha_2\beta_1$ integrin interaction induces osteoblastic differentiation in multipotent bone marrow stromal cells.

An $\alpha_2\beta_1$ integrin ligand is a substance that binds to $\alpha_2\beta_1$ integrin and optionally activates or inhibits a signal transduction pathway by binding to $\alpha_2\beta_1$ integrin, for example activating a transcription factor.

An $\alpha_5\beta_1$ ligand is a substance that binds to $\alpha_5\beta_1$ integrin and optionally activates or inhibits a signal transduction pathway by binding to $\alpha_5\beta_1$ integrin, for example activating a transcription factor. A representative $\alpha_5\beta_1$ integrin ligand includes, but is not limited to FNIII$_{7-10}$.

The ligand can be a peptide, antibody, or a small organic molecule that specifically binds to the specific integrin. A small organic molecule refers to a carbon-based molecule having a molecular weight of about 500 daltons or less. The antibody or an integrin binding fragment thereof can be single chained, humanized, or chimeric. In certain embodiments, the ligand can be a collagen-mimetic peptide, for example a stable triple-helical, collagen-mimetic peptide that contains the GFOGER (SEQ ID NO:12) adhesion motif from type I collagen that is recognized by the $\alpha_2\beta_1$ integrin. Circular dichroism analysis demonstrated that this peptide adopts a stable triple-helical conformation similar to the native structure of type I collagen. An exemplary collagen-mimetic peptide has the following amino acid sequence GGYGGGPC(GPP)$_5$GFOGER(GPP)$_5$GPC (SEQ ID NO:1, also referred to herein as "GFOGER peptide") or a variant thereof. Variants include peptides having conservative amino acid substitutions. Conservative substitutions refer to changes in amino acid sequence which have little or no effect on the function of the peptide.

In another embodiment, the $\alpha_2\beta_1$ integrin ligand has a sequence with at least 70% sequence identity, or preferably 80%, or more preferably 85% sequence identity to the reference sequence, or most preferably 90% identity to GGYGGGPC(GPP)$_5$GFOGER(GPP)$_5$GPC (SEQ ID NO:1).

Another embodiment provides an $\alpha_5\beta_1$ integrin ligand having at least 70% sequence identity, or preferably 80%, or more preferably 85% sequence identity to the reference sequence, or most preferably 90% identity to FNIII$_{7-10}$ (SEQ ID NO:2). FNIII$_{7-10}$ is a fibronectin fragment spanning the 7-10th type III repeats of fibronectin. The sequence of fibronectin is known in the art, see for example Baron, M. et al. (1992). 1H NMR Assignment and Secondary Structure of the Cell Adhesion Type III Module of Fibronectin. 31: 2068-2073; Baron, M. et al. (1990). Structure of the Fibronectin Type I Module. Nature. 345: 642-646; Ffrench-Constant C. (1995). Alternative Splicing of Fibronectin—Many Different Proteins but Few Different Functions. Exp. Cell. Res. 221: 261-271; Main, A L et al. (1992). The Three-Dimensional Structure of the Tenth Type III Module of Fibronectin: An Insight into RGD-Mediated Interactions. Cell. 71: 671-678. Potts, J R and Campbell, I D. (1994). Fibronectin Structure and Assembly. Curr. Cell Bio. 6: 648-655; Potts, J R and Campbell, I D. (1996). Structure and Function of Fibronectin Modules. Matrix Bio. 15: 313-320.

B. Devices

The disclosed devices include implants, rods, pins, screws, braces, plates, prosthesis, tissue engineering scaffolds, or the like. The device can be used for joining or fusing parts of one or more bones, joining tissue to bone, or joining tissue to tissue. The implants can also contain segments prepared from natural materials, synthetic materials (including polymers and ceramics), metals, metal alloys, or a combination thereof. In one embodiment, the implant is made of titanium. As used herein, "natural material" means "bone" and includes bone harvested from humans or animals. "Bone" may further include heterologous, homologous and autologous (i.e., xenograft, allograft, autograft) bone derived from, for example, fibula, tibia, radius, ulna, humerus, cranium, calcaneus, tarsus, carpus, vertebra, patella, ilium, etc. Bone may further include one or more bone products which have been partially or completely demineralized, prepared for transplantation (e.g., via removal of immunogenic proteins), and/or processed by other techniques. Additionally, the implants can be prepared from products made from bone, such as chips, putties, and other similar bone products. In some embodiments, human source bone is preferred for human applications.

Another embodiment provides a surface of a device, for example an implant, functionalized with an integrin-specific ligand for example, GFOGER (SEQ ID NO:12) or a FNIII$_{7-10}$ recombinant fragment that presents the RGD and PHSRN (SEQ ID NO:11) motifs in the biologically correct, i.e., as presented in the naturally occurring protein in vivo, structural context. These devices exhibit significantly higher adhesion strengths, FAK activations, and cell proliferation rates relative to supports presenting RGD or RGD-PHSRN (SEQ ID NO:4) oligopeptides. Moreover, FNIII$_{7-10}$-functionalized surfaces display specificity for $\alpha_5\beta_1$ integrin, while cell adhesion to surfaces presenting RGD or RGD-PHSRN (SEQ ID NO:4) is primarily mediated by $\alpha_V\beta_3$ integrin.

In other embodiments the substrate or device can include additional therapeutic agents including, but not limited, to growth factors, cytokines, morphogens, stem cells, umbilical cord stem cells, embryonic stem cells, adult stem cells, pluripotent cells derived from bone marrow, bone marrow stem cells, osteoblasts, osteoclasts, or a combination thereof. The cells can be autologous or heterologous. Growth factors include, but are not limited, to the TGF superfamily of growth factors, FGF, basic FGF, VEGF, insulin-like growth factor, EGF, PDGF, and nerve growth factor. Cytokines include but are not limited to IL-1 through IL-13.

II. Methods of Use

Substrates or devices having an $\alpha_2\beta_1$ integrin agonist, an $\alpha_5\beta_1$ integrin agonist, or a combination thereof can be used to treat or repair damaged or missing tissue. Tissues that can be treated include but are not limited to bone, orthopaedic, dental, cardiovascular, skin, liver, or kidney tissue. For example, implants having an $\alpha_2\beta_1$ ligand or an $\alpha_5\beta_1$ integrin ligand coating can be used to repair fractured or broken bones, to fuse or replace bones, or to improve the integration of an implant into existing bone tissue. Dental implants can be used to treat or repair damaged or missing teeth, and facial bones. In certain embodiments, the dental implant can be entirely for aesthetic purposes. In addition, implants can be use as a filler to augment or form dental tissue as to support the function of natural tissues (such as teeth or bone) or artificial prosthesis. The device can be configured for implantation into bone, orthopaedic, dental, cardiovascular, liver, or kidney tissue.

Another embodiment provides a method for improving implant integration relative to a control by coating a surface of an implant with an $\alpha_2\beta_1$ integrin agonist, an $\alpha_5\beta_1$ integrin agonist, or a combination thereof and implanting the coated implant into tissue of a patient, for example bone tissue. The amount of integrin ligand applied to the surface can vary depending on the desired outcome.

The implant can be coated with an amount of an $\alpha_2\beta_1$ or $\alpha_5\beta_1$ integrin ligand sufficient to promote or induce density-dependent cell adhesion, focal adhesion kinase signaling, cell differentiation, or a combination thereof. The $\alpha_2\beta_1$ or $\alpha_5\beta_1$ integrin ligand can be passively adsorbed to the implant for example by incubating the implant in 20 µg/ml in Dulbecco's phosphate-buffered saline (PBS) for about 1 hour. Alternatively, the $\alpha_2\beta_1$ or $\alpha_5\beta_1$ integrin ligand can be suspended in a vehicle and applied to the implant. Typically, the vehicle is a pharmaceutically acceptable vehicle that contains a binding agent, for example a gel or thickener, that causes the integrin ligand to adsorb or adhere to the surface of the implant.

In other embodiments the disclosed devices and implants can be used to treat bone disorders including, but not limited to, bone fractures, bone degeneration, osteoporosis, broken bones, spinal injuries, chipped bones, herniated vertebral discs, skull fractures, etc. The devices can also be used to treat dental disease including dental diseases that cause loss of teeth or loss of bone.

One embodiment provides a method for increasing osseointegration of prosthetics, devices, screws, pins, tissue-engineered constructs, scaffolds, and the like by coating one or more surfaces of the device with one or more integrin agonists, for example GFOGER (SEQ ID NO:12), $FNIII_{7-10}$, or a combination thereof.

Another embodiment provides a method for treating a bone defect, bone disorder or bone disease by implanting a device into a bone of a host wherein the device is coated with an amount of integrin ligand effective to promote bone growth. A host includes vertebrates, in particular mammals such as humans. In certain embodiments, the device is a scaffold, for example a polycaprolactone scaffold passively adsorbed with GFOGER (SEQ ID NO:12) or $FNIII_{7-10}$. The scaffold need not have cells or growth factors included. For example autologous bone forming cells or BMP proteins are not required, but could be included to augment activity, to have increased bone growth compared to controls. In certain embodiments, the device increases bone growth, bone regeneration, and or bone volume by about 5%, 10%, 15%, 20%, 25%, 30%, 35%, 40%, 45%, 50%, 55%, 60%, 65%, 70%, or 75% or more compared to a control. An exemplary control is a device without a coating of an integrin specific ligand such as GFOGER (SEQ ID NO:12) or $FNIII_{7-10}$.

Still another embodiment provides a method for adjusting the ability of a device to promote bone growth or osseointegration by varying the surface density of integrin-specific ligand on the device. Increasing the surface density of the integrin-specific ligand increases the ability of the device to promote bone growth or osseointegration compared to devices having a lower surface density of the integrin-specific ligand. Similarly, decreasing the surface density of the integrin-specific ligand on the device decreases the ability of the device to promote bone growth or osseointegration. By varying the surface density of the integrin-specific ligand, devices can be tailored to the needs of a specific patient to obtain the amount of bone growth or osseointegration needed by the patient.

Another embodiment provides a method of directing cell function, for example adhesion, proliferation, or differentiation in vitro by contacting the cell with a substrate coated with the disclosed integrin-specific ligands. Specific cell functions can be trigged by using substrates having integrin-specific ligands that trigger the desired cell function. Cell-based arrays having a substrate with addressable areas having integrin-specific ligands can be used to assay for pharmaceutical and or pathogen/toxins that modulate a cell function triggered by the integrin-specific ligand.

III. Methods of Manufacture

The disclosed devices can be made by passively adsorbing an integrin-specific ligand onto a surface of a device. For example, a peptide ligand can be prepared using conventional solid phase t-Boc synthesis. 20 µg/ml of the peptide ligand can be suspended in Dulbecco's phosphate-buffered saline (PBS) and incubated on the titanium surfaces for 1 h at 22° C.

Alternatively, the agonists can be attached to a surface of the device via a linker. Suitable linkers include, but are not limited to self-assembled monolayers (SAMs) of alkanethiols. Mixed alkanethiol SAMs presenting well-defined anchoring groups (—COOH) can be used for controlled tethering of ligands in a protein adsorption-resistant background (tri(ethylene glycol groups): $EG_3$). Peptides can be tethered via free amines using NHS/EDC coupling chemistry. For example GFOGER (SEQ ID NO:12) or $FNIII_{7-10}$ can be tethered onto activated/unactivated SAMs with $EG_6$-COOH:$EG_3$. A suitable $EG_6$-COOH:$EG_3$ solution ratio of 0.02 can be used.

Alternatively, the ligand can be tethered to ceramic or protein coatings on the implants.

Methods and Materials
Cell Isolation and Culture

Primary bone marrow stromal cells were harvested from the femora of young adult male Wistar rats in accordance with an IACUC-approved protocol. After excision, hindleg femora and tibiae were cleared of soft tissue and rinsed in growth medium (a-minimal essential medium supplemented with 10% fetal bovine serum, 1% penicillin-streptomycin, and 0.3 µg/ml amphotericin B). The ends of the long bones were then removed and the marrow space was flushed with culture medium (3-5 ml), using a syringe with an 18-gauge needle. Marrow isolates were pooled, centrifuged, resuspended in growth medium, and seeded for adhesion-dependent selection on tissue culture polystyrene dishes. Non-adherent hematopoietic cells were removed during subsequent medium exchanges, which occurred every other day. Cells were subcultured every two days according to standard techniques. For in vitro osteogenic assays, cells were seeded at 10,000 cells/cm² in growth medium. After 24 h, cultures were maintained in osteogenic medium consisting of growth medium supplemented with 50 μg/ml L-ascorbic acid and 3 mM sodium β-glycerophosphate.

Bacterial and mammalian cell culture reagents, Dulbecco's phosphate buffered saline (DPBS) and human plasma fibronectin (pFN) were obtained from Invitrogen (Carlsbad, Calif.). Fetal bovine serum (FBS) was acquired from Hyclone (Logan, Utah). "RGD peptide" (GRGDSPC) (SEQ ID NO:3) was purchased from BACHEM (San Diego, Calif.), and "RGD-PHSRN peptide" (GRGDG$_{13}$PHSRN, SEQ ID NO:4) peptide was synthesized by the Emory University Microchemical Facility (Atlanta, Ga.). Peptide tethering reagents, N-hydroxysuccinimide (NHS) and N-(3-dimethylaminopropyl)-N-ethylcarbodiimide hydrochloride (EDC), lysozyme and DNase were obtained from Sigma-Aldrich (St. Louis, Mo.). DH5a and JM109 bacterial cells were purchased from Invitrogen and Promega (Madison, Wis.), respectively. The XA3 Pinpoint Vector biotinylation expression system and ECF substrate were obtained from Promega and Amersham Pharmacia Biotech (Piscataway, N.J.), respectively.

Antibodies

Monoclonal HFN7.1 anti-human FN antibody was obtained from the Developmental Studies Hybridoma Bank (Iowa City, Iowa). Rabbit antibodies against alphaV (AB1930) and alpha5 (AB1921) integrin subunits were purchased from Chemicon (Temecula, Calif.), and anti-vinculin antibody (V284) was acquired from Upstate Biotechnology (Lake Placid, N.Y.). Function-perturbing hamster anti-rat beta1 integrin (Ha2/5), anti-mouse beta3 (2C9.G2), and anti-BrdU antibodies were purchased from BD Pharmingen. Alkaline phosphatase-conjugated donkey anti-mouse IgG (Jackson Immunoresearch, West Grove, Pa.) was used in enzyme linked immunosorbent assay (ELISA). AlexaFluor488-conjugated goat anti-mouse and anti-rabbit IgG antibodies, calcein-AM, and Hoechst 33258 dye were from Molecular Probes (Eugene, Oreg.). Monoclonal antibodies against total focal adhesion kinase (FAK) (Upstate Biotechnology) and specific phosphotyrosine residues in FAK (pY397, pY576) (BioSource International, Camarilla, Calif.) were used for FAK analysis. Biotinylated anti-rabbit IgG (Jackson Immunoresearch) and alkaline phosphatase-conjugated anti-biotin antibodies (BN-34, Sigma-Aldrich) were used for Western blotting.

Cell Lines

MC3T3-E1 murine immature osteoblast-like cells (Riken Cell Bank, Hirosawa, Japan) were used because of their expression of multiple integrins, including alpha5beta1, alpha2beta1, and alphaVbeta3. Cells were maintained at 37° C. in α-MEM supplemented with 10% FBS and 1% penicillin-streptomycin and passaged every 2-3 days via standard culture techniques.

In Vitro GFOGER Peptide (SEQ ID NO:1) Surface Preparation

The peptide GGYGGGPC(GPP)$_5$GFOGER(GPP)$_5$GPC (SEQ ID NO:1) [O=hydroxyproline] was prepared by the Emory University Microchemical Facility using solid phase t-Boc synthesis. Peptide was supplied in the purified form as a trifluoroacetic acid (TFA) salt and reconstituted at a stock concentration of 10 mg/ml in 0.1% TFA. For the in vitro assays, glass chamber slides (16-well Lab-Tek Chamber Slides, Nalge Nunc) or tissue culture-treated polystyrene dishes were coated with 300 Å of pure titanium using an electron beam evaporator at a chamber base pressure between 1-2×10$^{-6}$ torr with a deposition rate of 1.5 Å/second. The GFOGER peptide (SEQ ID NO:1) was diluted to 20 μg/ml in Dulbecco's phosphate-buffered saline (PBS) and incubated on the titanium surfaces for 1 h at 22° C.

Cell Adhesion Assay

Cell adhesion to functionalized and untreated titanium surfaces was measured using a centrifugation assay that applies controlled detachment forces. Titanium-coated glass chamber slide wells were reassembled using a silicone-based adhesive and coated with 20 μg/ml GFOGER peptide (SEQ ID NO:1) or 20 μg/ml GRGDSPC (SEQ ID NO:3) peptide (BACHEM). Control titanium slides were coated with 10% FBS (to model serum protein adsorption) or blocking buffer (5% non-fat dry milk in PBS to produce a non adhesive support). Stromal cells were loaded with the fluorescent dye calcein-AM (2 μg/ml, Molecular Probes), detached using trypsin+EDTA, and resuspended serum-free in PBS with 2 mM dextrose. Cells were seeded onto the substrates (10,000 cells/well) for 1 h at 37° C. For blocking experiments, cells were incubated in the presence of 20 μg/ml anti-rat α$_2$ antibody (hamster anti-rat CD49b monoclonal antibody, clone Ha1/29, BD Pharmingen) or 20 μg/ml anti-rat α$_v$ antibody (mouse anti-rat integrin α$_v$ chain monoclonal antibody, clone 21, BD Pharmingen). Isotype control antibodies had no effect on cell adhesion (data no shown). Initial fluorescence intensity was measured to quantify the number of adherent cells prior to application of centrifugal force. After filling the wells with PBS/dextrose and sealing with transparent adhesive tape, substrates were inverted and spun at a fixed speed in a centrifuge (Beckman Allegra 6, GH 3.8 rotor) to apply a centrifugal force corresponding to 12 g. After centrifugation, media was exchanged and fluorescence intensity was read to measure remaining adherent cells. For each well, adherent cell fraction was calculated as the ratio of post-spin to pre-spin fluorescence readings.

Osteoblast-Specific Gene Expression

Gene expression was analyzed by qRT-PCR. Total RNA was isolated at 7 days in culture using the Qiagen RNeasy RNA isolation kit. During RNA isolation and purification, samples were treated with DNaseI (27 Kunitz units/sample) for 15 min at room temperature to eliminate any genomic DNA contamination. The concentration of purified RNA was quantified using a NanoDrop™ (NanoDrop Technologies) and 1 μg of total RNA was used to synthesize cDNA templates by oligo(dT) priming using the Superscript First-Strand cDNA Synthesis System™.

qRT-PCR was performed with the ABI Prism 7700 Sequence Detection System (Applied Biosystems; 40 cycles; melting for 15 s at 95° C.; annealing and extending for 60 s at 60° C.) using SYBR Green DNA intercalating dye. Gene transcript concentration in the sample cDNA template solutions was quantified by preparing a functional range of dilutions from an absolute standard for each gene. Linear standard curves were then generated by plotting the log of the known concentration versus the $C_T$ value (the cycle number at which the fluorescence reached a threshold level). Oligonucleotide primers (Table 1) were designed using Primer Express™ software (Applied Biosystems).

TABLE 1

| Gene/Gen Bank Accession Number | Forward Primer | Reverse Primer |
|---|---|---|
| Runx 2/NM009820 | 5'-GGCCTTCAAGGTTGTAGCCC-3'<br>SEQ ID NO: 5 | 5'-CCCGGCCATGACGGTTA-3'<br>SEQ ID NO: 6 |
| OCN/X04141 | 5' ACGAGCTAGCGGACCACATT-3'<br>SEQ ID NO: 7 | 5'-CCCTAAACGGTGGTGCCATA-3'<br>SEQ ID NO: 8 |
| BSP/J04215 | 5'-TGACGCTGGAAAGTTGGAGTT-3'<br>SEQ ID NO: 9 | 5'-GCCTTGCCCTCTGCATGTC-3'<br>SEQ ID NO: 10 |

Alkaline Phosphatase Biochemical Activity and Calcium Incorporation Assays

ALP activity was quantified at 7 days in culture using a modification of the Sodek and Berkman method. Briefly, cells were rinsed with PBS and scraped in cold 50 mM Tris-HCl. After sonication and centrifugation, the protein concentration was quantified using a Pierce Micro BCA protein assay kit. Equal amounts of protein (2.5 µg) were added to 60 µg/ml 4-methyl-umbelliferyl-phosphate fluorescent substrate in diethanolamine buffer (pH 9.5). After a 60 min incubation at 37° C., the fluorescence was read at an excitation of 360 nm and an emission of 465 nm on an HTS 7000 Plus BioAssay Reader (Perkin Elmer). Enzymatic activity was standardized using purified calf intestinal alkaline phosphatase.

Calcium content was determined by dissolving mineralized deposits with 1 N acetic acid overnight. Appropriately diluted sample (25 µl) was added to 300 µl of arsenazo III-containing Calcium Reagent (Diagnostic Services Ltd). The absorbance of the resulting samples was measured at 650 nm and compared to a linear standard curve of $CaCl_2$ in 1 N acetic acid.

Tibial Implantation Procedure

Commercially pure titanium implants (FIG. 4) were sonicated in de-ionized water for 20 min to remove surface debris. Implants were then dipped in 4% HF for 30 sec to remove the existing oxide layer and then incubated in 35% $HNO_3$ for 30 min at 50° C. to regenerate a new oxide coating. Samples were transferred to 1.8 N NaOH for 1 min to terminate the oxidation reaction. Implants were then rinsed and boiled in de-ionized water for 1 h. To create the bioactive coating, the implants were incubated in 20 µg/ml GFOGER peptide (SEQ ID NO:1) or type I collagen solution for 1 h. Control titanium rods were incubated in PBS.

Implantations were conducted in accordance with an IACUC-approved protocol. Both hind legs of anesthetized, mature Sprague-Dawley male rats (250-350 g) were shaved and scrubbed with alcohol. The medial aspect of the proximal tibial metaphysis was exposed through an antero-medial skin incision, leaving the medial collateral ligament intact. Using a saline-cooled drill, two defects were created in each tibia. Sterile implant rods were press fit into the defects. Periosteum was mobilized and sutured over the implantation site, and the skin was closed with wound clips. Subjects were euthanized after 4 weeks and proximal tibiae were fixed in neutral buffered formalin for histology or recovered without fixation and maintained in PBS-moistened gauze for immediate mechanical testing.

Based on power calculations and previous reports in the literature, it was estimated that a minimum of eight implants per experimental group are required to detect differences of 10% in mechanical testing and a minimum of four implants per experimental group are required for histomorphometry for a total of 11 implants per experimental group. In this model, each animal receives four implants, two in each tibia. The sample conditions were distributed according to a randomized block design, in which the three conditions were randomized according to proximal/distal and left/right tibia placement, but were constrained into blocks containing one each of the conditions. A total of 12 animals with 16 implants per condition were used—seven for histology and nine for mechanical testing. One additional animal with one implant per condition was included as an extra in the event of tibia breakage during harvest or during the apparatus set-up for mechanical testing.

Histomorphometry Analyses and Mechanical Testing

Excised tibiae were fixed in 10% neutral buffered formalin for 1 week. The formalin-fixed tibiae were dehydrated in a graded series of alcohol incubations and then embedded in poly(methyl methacrylate). Ground sections of 50-80 µm were generated using the Exakt Grinding System™. Two longitudinal ground sections were generated per tibia, each containing two titanium plugs inserted transverse to the tibia's long axis. Sections were then stained with Sanderson's Rapid Bone Stain™ and a van Gieson counter stain. Bone implant contact (BIC) was measured as the percentage of implant's circumference that was in direct contact with bone tissue (Adobe Photoshop® CS imaging software).

Implant mechanical fixation to the bone was measured with a pull-out force test using a biomechanical testing apparatus (EnduraTEC Bose ELF 3200). The ends of each excised tibia were secured in a custom designed holding apparatus with the exposed head of each implant facing in the direction of the pull motion and centered along the axis of motion. A 0.014" diameter piano wire was threaded through the implant head and both wire ends attached firmly to an 11 lb. INTERFACE load cell. Samples were pre-loaded with 2 N to ensure proper and identical wire tautness among implants. Tests were performed at a constant force rate of 0.2 N/sec using WINTEST application software. The direction of the pull was parallel to the long axis of the implant. The pull-out force (N) was the maximum load achieved before failure and was determined from the recorded load vs. displacement data.

Recombinant $FNIII_{7-10}$ Production

A monobiotinylated FN fragment spanning the 7-10th type III repeats of FN, $FNIII_{7-10}$, was produced using standard recombinant DNA techniques. cDNA encoding for human $FNIII_{7-10}$ was ligated into the XA3 plasmid (Pinpoint System, Promega). See for example, S. M. Cutler and A. J Garcia. (2003) *Engineering cell adhesive surfaces that direct intergin alpha5beta1 binding using a recombinant fragment of fibronectin*, Biomaterials, 24:1759-70. The resulting construct, encoding for $FNIII_{7-10}$, with a biotin tagging sequence at the amine terminus, was amplified in DH5α cells, purified, and sequenced. JM109 bacterial cells were transformed with the plasmid and streaked onto LB agar plates containing 100 µg/ml ampicillin and incubated overnight. Colonies were isolated and dynamically cultured in LB broth (100 µg/ml ampicillin; 2 µm d-biotin). At 6 h, 100 µM IPTG was added to augment protein production. The cell broth was spun down at 8000 g for 10 min at 4° C., and the cell pellet was resuspended at 10 ml/g of cell paste in lysis buffer (50 mM Tris-HCl pH 7.5, 50 mM NaCl, 5% glycerol). Lysozyme (1 mg/ml) was added at 4° C. to the cell suspension and stirred for 20 min, then sodium deoxycholate (1 mg/ml) for 5 min, and finally DNase I (40 µg/ml) for another 10 min. The lysate was centrifuged (10,000 g) for 20 min. The protein supernatant was sterile-filtered, and purified by affinity chromatography using a 5 ml column of Ultralink Immobilized Monomeric Avidin (Pierce) connected to a gradient pump, UV monitor, and fraction collector (BioRad, Hercules, Calif.). Briefly, after sequential column washes with regeneration and elution buffers, the protein solution was allowed to bind to the column for 1 h at a 0.4 ml/min flow rate. After washing with DPBS, elution buffer (0.5 mg/ml d-biotin in DPBS) was flowed through (1 ml/min) and the eluted fractions monitored for protein. Protein fractions were filtered using 30 kDa Microcon centrifugal filter devices (Millipore, Bedford, Mass.) to remove d-biotin, and verified as >98% pure $FNIII_{7-10}$ by Western blotting. Purified samples were flash frozen for storage (−80° C.).

Model Biomaterial Surfaces

Self-assembled monolayers (SAMs) of alkanethiols on gold were used to present well-defined, ordered surfaces with anchoring groups within a non-fouling background. Tri(ethylene glycol)-terminated alkanethiol ($HS-(CH_2)_{11}-(OCH_2CH_2)_3-OH$; $EG_3$) and carboxylic acid-terminated alkanethiol ($HS-(CH_2)_{11}-(OCH_2CH_2)_6-OCH_2COOH$; $EG_6$-COOH) were previously synthesized and characterized. Gold-coated substrates were prepared by sequential deposition of titanium (100 Å) and gold (200 Å) films via an electron beam evaporator (Thermionics Laboratories, Hayward, Calif., $2\times10^{-6}$ Torr, 1 A/s) onto clean 6-well plate lids or glass coverslips. Mixed SAM surfaces were prepared on substrates by immersing in a 1.0 mM mixed solution of $EG_3/EG_6$-COOH thiols (4 h). Peptide ligands were tethered using standard peptide chemistry. Briefly, following washing in ethanol and ultrapure $H_2O$, SAMs were incubated in 2.0 mM EDC and 5.0 mM NHS in 0.1 M 2-(N-morpho)-ethanesulfonic acid and 0.5 M NaCl (pH 6.0), and subsequently immersed in a 20 mM solution of 2-mercaptoethanol in deionized $H_2O$. Adhesive ligands in PBS were then incubated on the activated supports for 30 min and the unreacted surface NHS esters were then quenched in 20 mM glycine. Finally, the surfaces were blocked in 1% heat-denatured bovine serum albumin (BSA) and then incubated overnight in DPBS to reduce nonspecific protein adsorption.

ELISA and Surface Density Measurements

An ELISA was used to probe for the biological activity of the $FNIII_{7-10}$ fragment compared to pFN. $FNIII_{7-10}$ or pFN was adsorbed onto either uncoated or Neutravidin-coated (100 µg/ml) 96-well black U-well Dynex plates at various concentrations for 30 min. Following incubation in blocking buffer (0.25% BSA, 0.1 M EDTA, 2.5% Tween-20, 0.00125% $NaN_3$), HFN7.1 antibody (0.6 µg/ml in blocking buffer) was added for 1 h at 37° C., and, after washing with blocking buffer, surfaces were incubated in alkaline phosphatase-conjugated anti-mouse IgG (0.6 µg/ml) for 1 h at 37° C. Washed surfaces were exposed to 4-methylumbelliferyl phosphate (25 mg/ml in 10 mM diethanolamine, pH 9.5). The resulting fluorescence was quantified using an HTS 7000 Plus plate reader (Perkin Elmer, Foster City, Calif.) at 360 nm excitation and 465 nm emission.

Surface density measurements were obtained via surface plasmon resonance (SPR) using a Biacore X instrument (Biacore, Piscataway, N.J.). Mixed SAM surfaces were prepared as described above on Au-coated STA chips (Biacore), primed with sterile DPBS, and the baseline allowed to stabilize at a flow rate of 15 µl/min in DPBS. Ligands were tethered by activating the surface with NHS/EDC for 10 min at a 10 µl/min flow rate, and ligand solutions were subsequently injected at a flow rate of 4 µl/min for 30 min. Finally, surfaces were washed with 20 mM glycine at 10 µl/min and the signal was allowed to stabilize for 2 min thereafter to measure tethered peptide levels. To assay for the relative degree of biotinylation, a solution of $FNIII_{7-10}$ was flowed over a streptavidin chip at 20 µl/min for 4 min. Resonance units (RU) were converted to surface density values (10 RU=1 $ng/cm^2$).

Centrifugation Cell Adhesion Assay

A modification of a centrifugation assay was used to apply controlled detachment forces to cells adhering to engineered surfaces. Multi-wells of engineered surfaces were created on gold-coated polystyrene plate lids using silicone gaskets (Grace Bio-Labs, Bend, Oreg.). Mixed SAMs were assembled and ligands tethered at varying densities. MC3T3-E1 cells were labeled with 4 mM calcein-AM, a membrane-permeable green fluorescent dye, in 2 mM dextrose-DPBS for 30 min and resuspended in α-MEM with 10% FBS. Cells were seeded onto the surfaces at 200 $cells/mm^2$, and allowed to attach for 1 h at 37° C. For blocking antibody experiments, cells were incubated in the presence of function-perturbing antibodies (10 µg/ml) for 10 min with gentle agitation prior to cell seeding. Before centrifugation, cell images were taken using a Nikon TE-300 fluorescence microscope and Spot RT digital camera. Wells were then filled completely with dextrose-PBS, sealed, inverted, and centrifuged for 5 min at a prescribed speed on a Beckman Allegra 6 centrifuge (GH 3.8 rotor) to apply normal detachment forces. Media was then gently aspirated from the wells, and wells were refilled for post-spin image collection. Post/pre-spin cell ratios were determined by image analysis, and this adhesive fraction was plotted against ligand surface density to obtain cell adhesion profiles.

Immunofluorescence Staining for Integrins and Focal Adhesions

Surfaces were prepared on either 6-well plate lids or 35 min tissue culture dishes, and cells seeded at 75 $cells/mm^2$ in serum-containing media for 4 h at 37° C. For integrin staining, a cross-linking/extraction biochemical method that selectively isolates bound integrins was employed. Cells were washed, and 1.0 mM DTSSP (Pierce) was added for 15 min to cross-link ligated integrins. After quenching with 5 0 mM Tris, uncrosslinked cellular components were extracted in 0.1% SDS supplemented with protease inhibitors (350 µg/ml PMSF). Samples were then blocked in 5% FBS for 1 h and incubated with integrin-specific antibodies for 1 h at 37° C. Fluorochrome-labeled secondary antibodies were then incubated for 1 h at 37° C. Following washing, samples were mounted on slides with Gel/Mount mounting media (Biomeda, Foster City, Calif.). For staining of focal adhesions, cells were extracted in 0.5% Triton X-100 in ice-cold cytoskeleton buffer (50 mM NaCl, 3 mM $MgCl_2$, 150 mM sucrose, 20 µg/ml aprotonin, 1 µg/ml leupeptin, 1 mM PMSF, 50 mM Tris, pH 6.8) for 2 min and fixed in cold 3.7% formaldehyde in DPBS for 5 min. Cultures were blocked, subsequently incubated in anti-vinculin monoclonal antibody (1:70 in 5% FBS) and fluorochrome-labeled secondary antibodies for 1 h, and samples mounted on slides.

FAK Phosphorylation

Cells were detached and gently agitated in serum-free suspension for 45 min to reduce background. Cells were then seeded at 200 $cells/mm^2$ serum-free for 1 h. Cells were lysed in RIPA buffer (1% Triton X-100, 1% sodium deoxycholate, 0.1% SDS, 150 mM NaCl, 150 mM Tris-HCl (pH 7.2), 350 μg/ml PMSF, 10 μg/ml leupeptin, and 10 μg/ml aprotonin) for 20 min on ice. Samples were pipetted up and down 20 times and centrifuged at 8000 g for 10 min to shear DNA and isolate protein contents. Total protein was quantified using micro-BCA (Pierce). Equal amounts of protein were boiled for 10 min in Laemmli buffer and separated by SDS-PAGE on a 7% gel, transferred to nitrocellulose membranes, and blocked with Blotto (5% nonfat dry milk, 0.20% Tween-20) overnight at 4° C. Membranes were gently rocked in antibodies against FAK and specific phosphorylated FAK tyrosine residues (anti-total FAK at 1 μg/ml, anti-FAK pY397 at 0.35 μg/ml, anti-FAK pY576 at 0.5 μg/ml) for 1 h. After washing with TBS-Tween (20 mM Tris HCl pH 7.6, 137 mM NaCl, 0.1% Tween-20), secondary antibody (biotin-conjugated anti-rabbit IgG; 1:20,000) was added for 1 h, followed by alkaline phosphatase-conjugated anti-biotin antibody (1:10,000) in Blotto. Immunoreactivity was assessed by ECF fluorescent substrate. FAK bands were visualized by a Fuji Image Analyzer and phosphorylation levels normalized to total FAK.

Cell Proliferation Rate

Cells were seeded on surfaces in 10% serum for 16 h, and BrdU (3.1 μg/ml) was added for the last 4 h. After washing with DPBS, samples were fixed in 70% cold ethanol for 10 mM, denatured in 4 M HCl for 20 mM, neutralized in 50 mM NaCl in 100 mM Tris-HCl (pH 7.4), washed, and blocked with 5% FBS+1% heat-denatured BSA. Cultures were incubated in anti-BrdU antibody (1:1000) and AlexaFluor488-conjugated anti-mouse IgG (1:200). Nuclei were counterstained with Hoechst dye (1:10,000). Fluorescent images were used to quantify the number of cells positive for BrdU relative to total cell nuclei using an in-house image analysis routine. Ten representative fields were analyzed per well with multiple wells for each surface condition.

Statistics

Data are reported as mean±standard error. Results were analyzed by one-way ANOVA using SYSTAT 8.0 (SPSS). If treatment level differences were determined to be significant, pair-wise comparisons were performed using a Tukey post-hoc test. A 95% confidence level was considered significant. All of the in vitro assays were performed as two separate experiments in triplicate.

Example 1

The Bioactive GFOGER (SEQ ID NO:1) Peptide Specifically Targets The $\alpha_2\beta_1$ Integrin To reproduce titanium implant surfaces in vitro, culture dishes were coated with a 300 Å titanium layer via electron beam evaporation. The GFOGER peptide (SEQ ID NO:1) was then passively adsorbed onto the titanium at a concentration of 20 μg/ml, creating the integrin-targeted bioactive coating. Surface plasmon resonance spectroscopy revealed a surface density of 123.2±6.2 ng/cm². Primary rat bone marrow stromal cells were used to validate this surface treatment strategy in vitro since this heterogeneous population contains osteoprogenitors and human bone marrow stromal cells are currently used in clinical applications. A centrifugation cell adhesion assay demonstrated greater stromal cell adhesion on the GFOGER-peptide (SEQ ID NO:1) surfaces compared to titanium surfaces pre-exposed to linear RGD peptide (SEQ ID NO:3) or serum (FIG. 1).

FIG. 1 shows cell adhesion is greater on adsorbed GFOGER peptide (SEQ ID NO:1) surfaces than untreated titanium (Ti) and is specific for the $\alpha_2\beta_1$ integrin. The data represent 1 h serum-free bone marrow stromal cell adhesion and subsequent centrifugation at 12 g for 5 min. Surfaces were adsorbed GFOGER peptide (SEQ ID NO:1) on Ti, adsorbed linear RGD peptide (SEQ ID NO:3), adsorbed fetal bovine serum (10% in PBS), and non-adhesive blocked Ti. Cells were seeded without antibody or in the presence of either anti-$\alpha_2$ or anti-$\alpha_v$ integrin blocking antibodies. ANOVA: $p<1E-9$; *GFOGER peptide (SEQ ID NO:1) w/o Ab>GFOGER peptide (SEQ ID NO:1) with anti-$\alpha_2$ ($p<6E-6$); #serum w/o Ab>serum with anti-$\alpha_v$ ($p<6E-6$).

Cell adhesion to the RGD-treated surface was equivalent to background levels observed on titanium blocked with non-adhesive proteins, reflecting the inability of this short peptide to passively adsorb onto titanium. Importantly, a blocking anti-$\alpha_2$ antibody completely eliminated cell adhesion to GFOGER peptide-treated (SEQ ID NO:1) surfaces, verifying the peptide's specificity for the $\alpha_2\beta_1$ integrin. However, this $\alpha_2\beta_1$ antibody had no effect on adhesion to serum-exposed titanium, demonstrating that stromal cell adhesion to untreated titanium is not mediated by $\alpha_2\beta_1$ integrin. Since untreated titanium adsorbs abundant RGD-containing serum proteins, such as vitronectin, adhesion to these surfaces most likely involves the $\alpha_v\beta_3$ integrin, which recognizes RGD in a wide variety of proteins and synthetic peptides. Indeed, a function-perturbing anti-$\alpha_v$ antibody had no effect on adhesion to the GFOGER peptide (SEQ ID NO:1) but completely blocked adhesion above background on the serum-exposed titanium. These results demonstrate that the bioactive GFOGER peptide (SEQ ID NO:1) specifically targets the $\alpha_2\beta_1$ integrin. These adhesion results also show that untreated titanium surfaces, which directly adsorb serum proteins, preferentially engage the $\alpha_v\beta_3$ integrin. Because GFOGER peptide (SEQ ID NO:1)-coated and control titanium surfaces each interact with unique integrins, these surfaces may recruit different cell populations at the implant site and/or have diverse effects on cellular maturation and bone formation in vivo.

Example 2

Figure 2A:
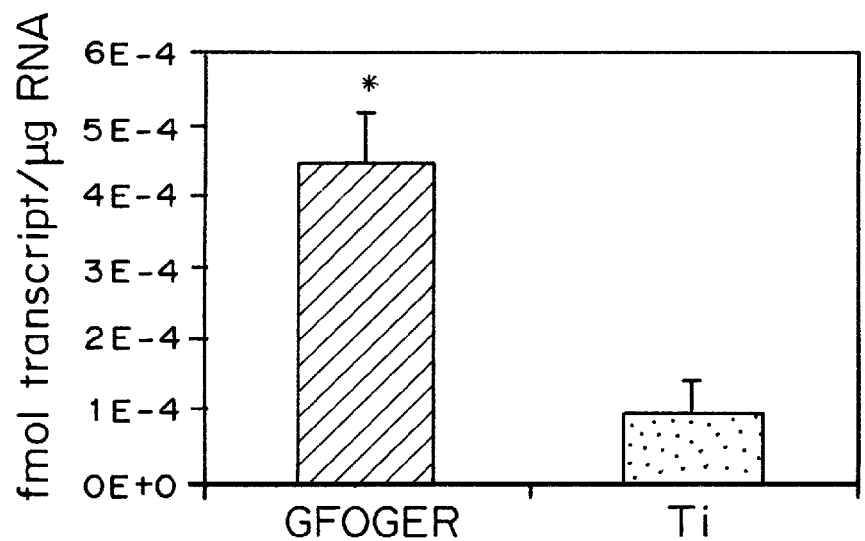
FIG. 2A is a bar graph showing amount of Runx2 mRNA expression (fmol transcription/μg) in cells cultured on GFOGER peptide (SEQ ID NO:1)-coated surfaces or Ti surfaces.
Figure 2B:
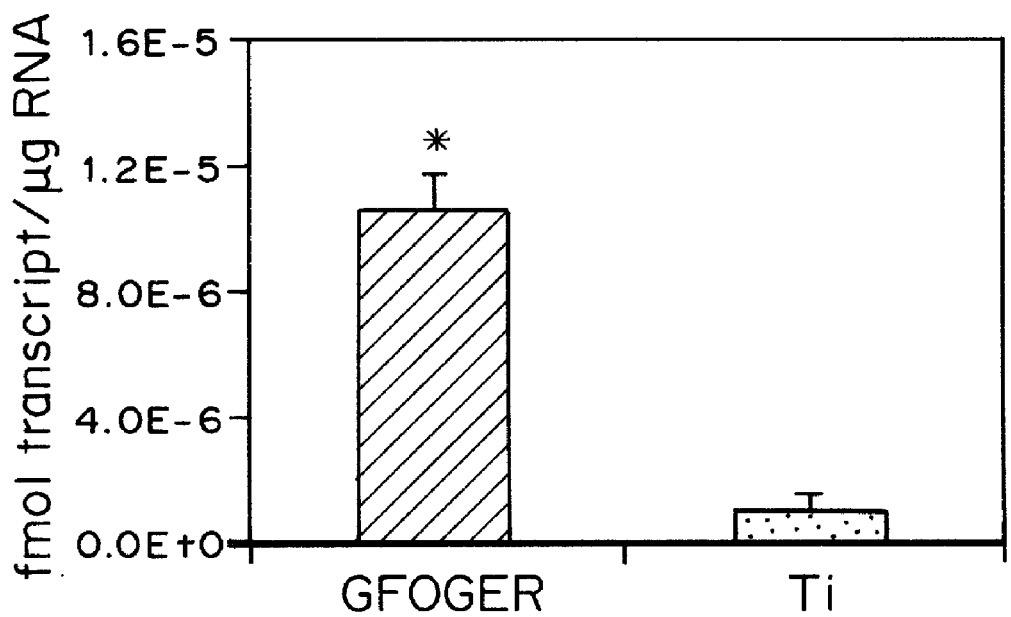
FIG. 2B is a bar graph showing amount of osteocalcin mRNA (fmol transcription/mg) in cells cultured on GFOGER peptide (SEQ ID NO:1)-coated surfaces or Ti surfaces.
Figure 2C:
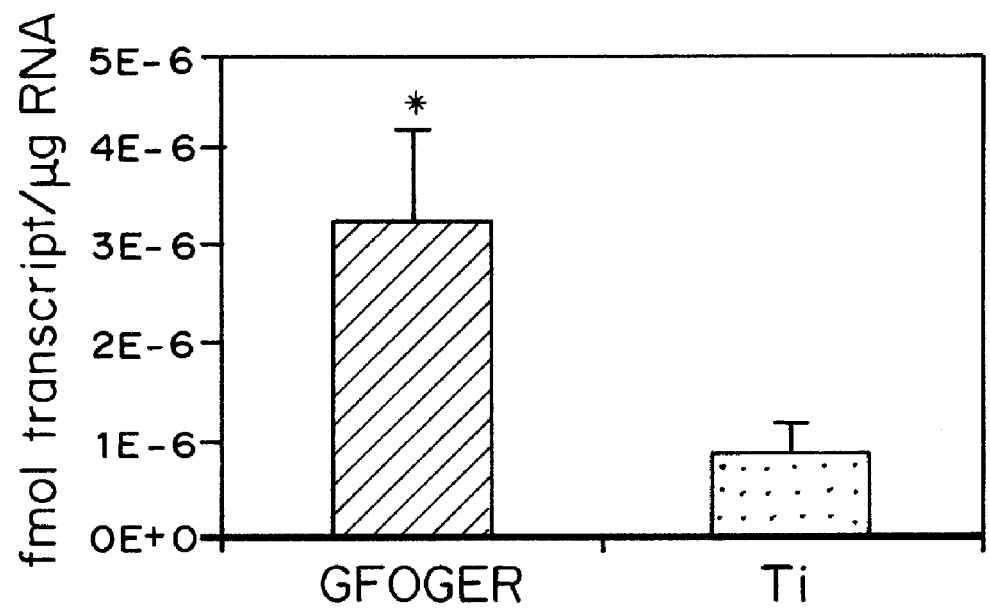
FIG. 2C is a bar graph showing amount of bone sialoprotein mRNA (fmol transcription/μg) in cells cultured on GFOGER peptide (SEQ ID NO:1)-coated surfaces or Ti surfaces.

Bioactive GFOGER-Peptide (SEQ ID NO:1) Surface Triggers The Transcriptional Machinery Necessary for Osteoblastic Differentiation To investigate the osteoblastic differentiation potential of these surfaces, quantitative RT-PCR (qRT-PCR) was used to probe osteoblast-specific gene expression in 7 day cultures of bone marrow stromal cells (FIGS. 2A-2C). The data represent osteoblast-specific gene expression measured by qRT-PCR for Runx2 transcription factor (FIG. 2A), osteocalcin (OCN) (FIG. 2B), and bone sialoprotein (BSP) (FIG. 2C) in rat bone marrow stromal cells cultured for 7 days on GFOGER peptide (SEQ ID NO:1) surfaces or untreated Ti. Runx2 ANOVA: *GFOGER peptide (SEQ ID NO:1)>Ti ($p<0.02$); OCN ANOVA: *GFOGER peptide (SEQ ID NO:1)>Ti ($p<0.002$); BSP ANOVA: *GFOGER peptide (SEQ ID NO:1)>Ti ($p<0.05$).

Expression levels of Runx2/Cbfa1, a transcription factor essential for bone formation and osteoblastic differentiation, were elevated on the GFOGER peptide (SEQ ID NO:1)-treated surfaces compared to untreated titanium (FIG. 2A). The upregulation of this key osteoblast-specific transcription factor demonstrates the ability of the bioactive GFOGER-peptide (SEQ ID NO:1) surface to trigger the transcriptional machinery necessary for osteoblastic differentiation (FIG. 2B). To determine whether this pattern of increased Runx2 gene expression parallels similar increases in the expression of other osteoblast-specific genes, the transcript levels of osteocalcin and bone sialoprotein were also examined. For both bone-specific markers, qRT-PCR revealed greater levels of gene expression on the GFOGER-peptide (SEQ ID NO:1) surfaces compared with untreated titanium (FIGS. 2A-2C). These results indicate that the $\alpha_2\beta_1$ integrin-targeted peptide promotes the expression of multiple genes specifically associated with a mature osteoblastic phenotype.

Figure 3A:
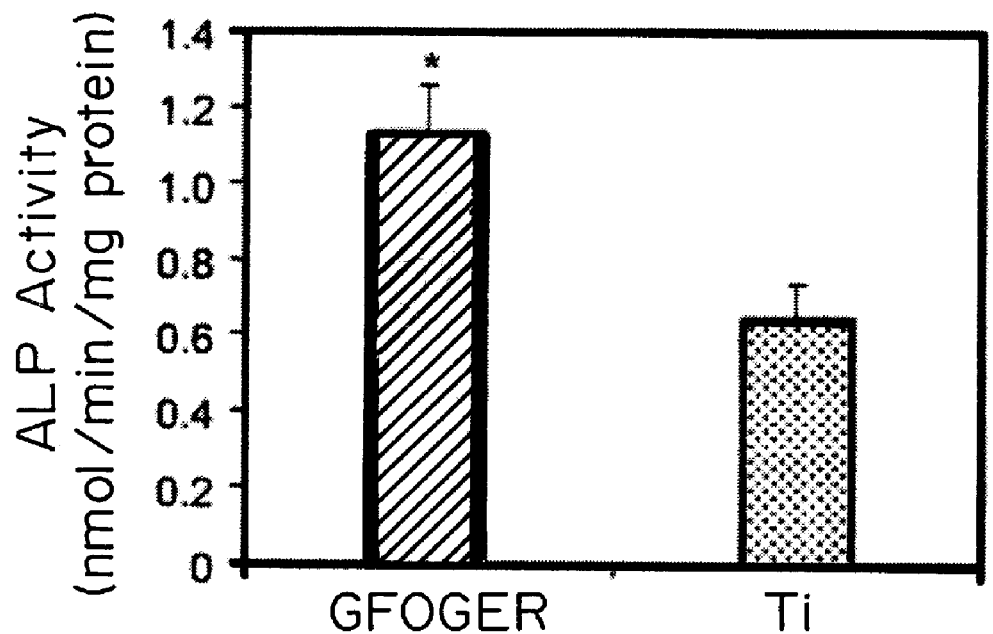
FIG. 3A is a bar graph showing alkaline phosphatase activity (nmol/min/mg protein) by cells cultured on GFOGER peptide (SEQ ID NO:1)-coated surfaces compared to cells cultured on uncoated titanium surfaces.

Osteoblastic differentiation is also characterized by the activation of multiple proteins, including alkaline phosphatase (ALP). The ALP enzyme is often used as a marker for osteoblastic metabolic activity and an early indicator of osteoblastic differentiation. An ALP biochemical assay revealed elevated levels of activation on the GFOGER-peptide (SEQ ID NO:1) coating compared to untreated titanium (FIG. 3A). Because ALP is the enzyme responsible for hydrolyzing phosphate esters and inducing bone mineralization, these results suggest that this bioactive surface treatment may also be capable of promoting enhanced bone matrix mineralization. ALP ANOVA: *GFOGER peptide (SEQ ID NO:1) >Ti ($p<0.02$).

Figure 3B:
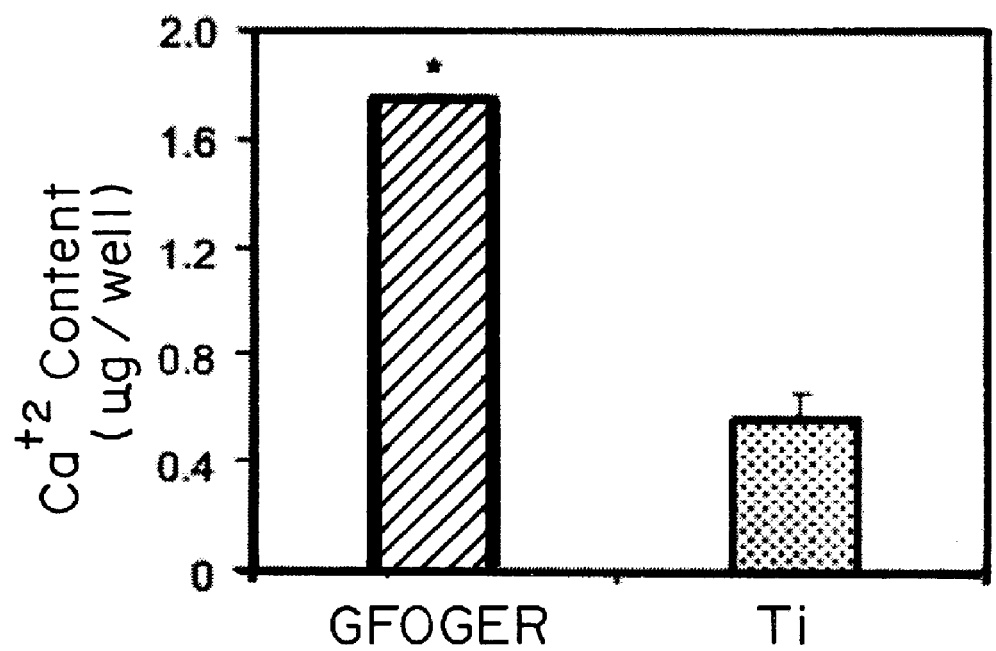
FIG. 3B is a bar graph showing $Ca^{+2}$ content (μg/well) in rat bone marrow stromal cultures on surfaces coated with GFOGER peptide (SEQ ID NO:1) or uncoated Ti surfaces.

Matrix mineralization was examined as an in vitro endpoint indicator of the osteoblastic phenotype in the bone marrow stromal cells. Calcium phosphate mineral deposition was examined after 14 days in culture using calcium content analysis. Cultures on GFOGER peptide-treated (SEQ ID NO:1) surfaces displayed a three-fold enhancement in calcium-based mineral deposition compared to untreated titanium (FIG. 3B). $Ca^{+2}$ ANOVA: *GFOGER peptide (SEQ ID NO:1)>Ti ($p<2E-4$). This enhanced capacity for mineralization on the peptide-treated surfaces is in excellent agreement with the observed up-regulation in osteoblast-specific gene expression and ALP activity. These results verify the advantageous effects of controlled $\alpha_2\beta_1$ integrin-binding on cell function, in this case osteoblastic differentiation and matrix mineralization.

Example 3

Figure 4:
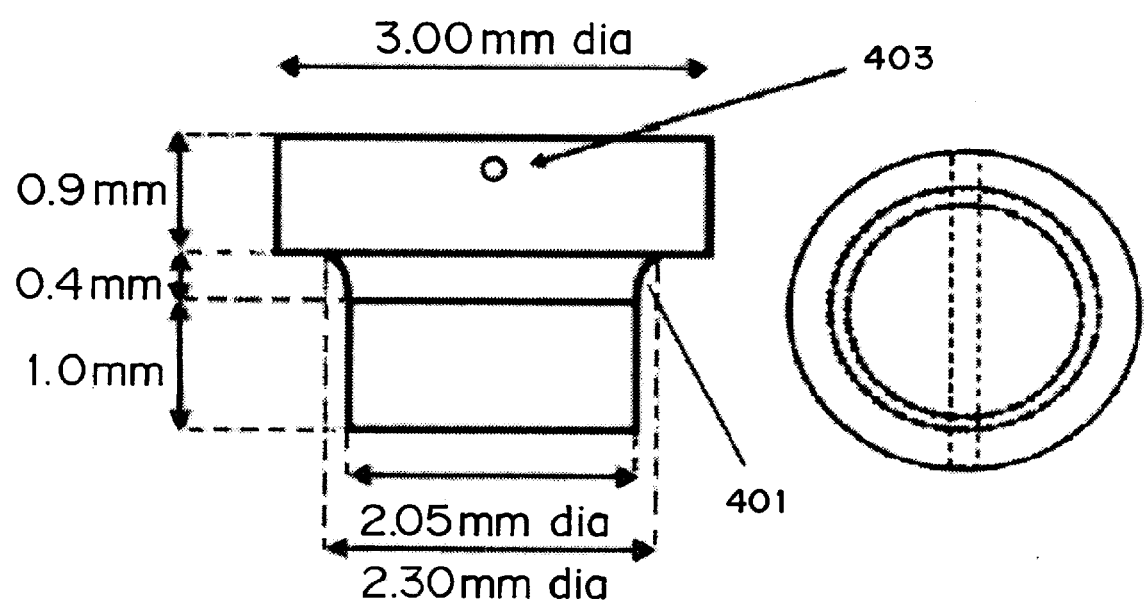
FIG. 4 is diagram of a representative cylindrical titanium implant rod with tapered stop collar (401) and transverse hole (403) for pull-out mechanical testing. The metal is ASTM F67 Grade 4 commercially pure titanium.

Integrin-Targeted GFOGER Peptide (SEQ ID NO:1) Surfaces Enhance In Vivo Osseointegration To evaluate the performance of the bioactive GFOGER peptide (SEQ ID NO:1) treatment in vivo, osseointegration in a rat tibia cortical bone model was quantified using quantitative histomorphometry and pull-out mechanical testing. A cylindrical titanium implant rod with a tapered stop collar was designed (FIG. 4). The tapered head ensures that all implants are inserted into the bone at the same depth, guaranteeing uniform bone contact among treatments. Using a saline-cooled drill, two defects 2 mm in diameter were created in the medial aspect of the proximal tibial metaphysis. Implant rods consisting of GFOGER peptide (SEQ ID NO:1) functionalized or untreated (control) titanium were press fit into the cortical defects. After four weeks, the rat tibiae were harvested and evaluated for bone apposition by histological staining and mechanical integration by pull-out testing. Histological sections revealed substantial and contiguous bone mineral along the periphery of GFOGER peptide (SEQ ID NO:1)-treated titanium implants. Representative micrographs show 50-80 µm longitudinal ground sections of rat tibia stained with Sanderson's Rapid Bone Stain™ and van Gieson counterstain. Cells stain dark to light blue, soft tissue elements stain blue-green, and bone matrix stains yellow orange to autumn orange.

Figure 5A:
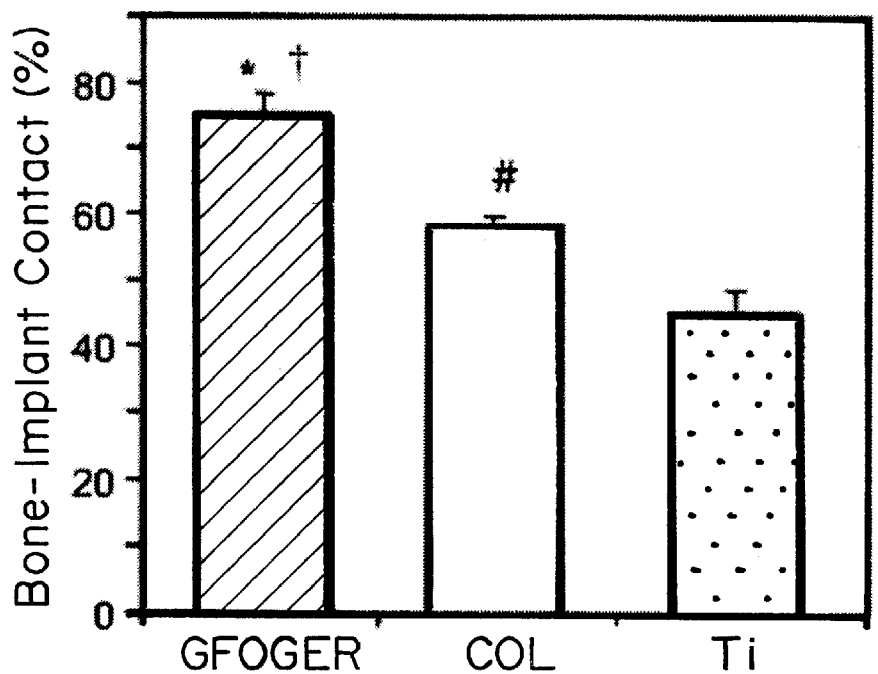
FIG. 5A is a bar graph showing percent bone-implant contact of GFOGER peptide (SEQ ID NO:1) treated; collagen treated or untreated control implants.

Less bone mineral was visible on surfaces treated with the native type I collagen, and the adjacent mineral appeared more porous. Significantly less mineral staining was present on untreated titanium and the mineral deposits appear in isolated patches along the surface of the implants. Image quantification to determine the percentage of the bone-implant apposition (bone implant contact, BIC) demonstrated a nearly two-fold enhancement in bone apposition on the GFOGER peptide (SEQ ID NO:1)-coated surfaces compared to untreated titanium (FIG. 5A). Bone apposition is measured as the percentage of implant's circumference that is in direct contact with bone mineral in the histological sections. ANOVA: $p<4E-6$, *GFOGER peptide (SEQ ID NO:1)>Ti ($p<0.002$), †GFOGER peptide (SEQ ID NO:1)>COL ($p<0.01$), #COL>Ti ($p<0.04$).

Figure 5B:
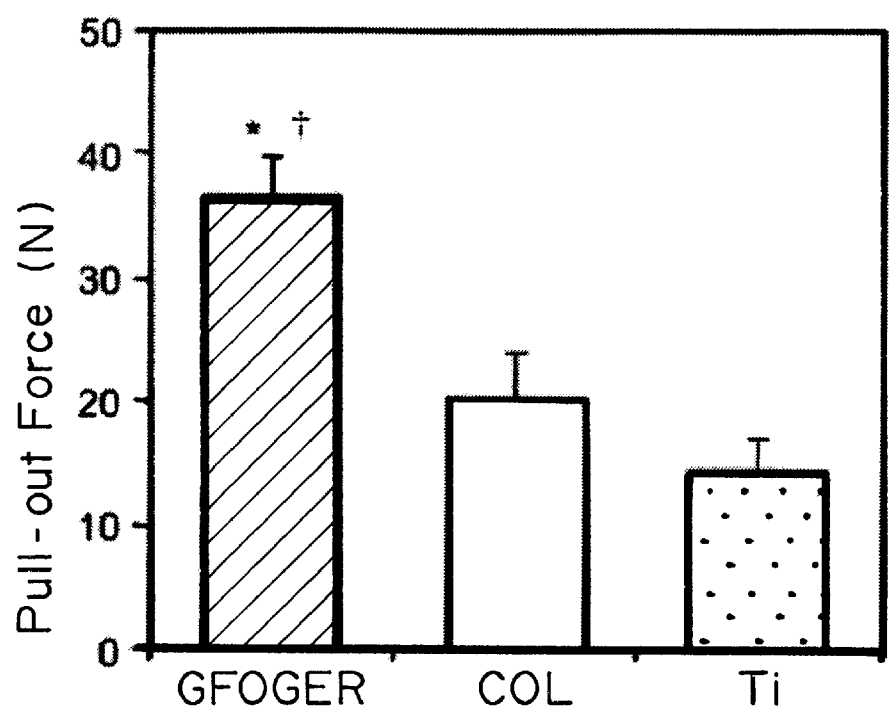
FIG. 5B is a bar graph showing pull-out force (N) of GFOGER peptide (SEQ ID NO:1)-treated, collagen-treated, or untreated control surfaces.

Pull-out mechanical testing indicated significantly higher mechanical fixation of the peptide-functionalized implants compared to type I collagen or untreated titanium (FIG. 5B). Osseointegration is measured as the maximum force [N] necessary to dislodge the implant in a pull-out test. ANOVA: $p<9E-7$, *GFOGER peptide (SEQ ID NO:1)>Ti ($p<0.0009$), †GFOGER peptide (SEQ ID NO:1)>COL ($p<0.01$).

These results demonstrate a greater quantity and continuity of peri-implant bone mineral on the integrin-targeted GFOGER peptide (SEQ ID NO:1) surfaces in viva as well as enhanced mechanical integrity and osseointegration. In addition, the biomimetic peptide induced greater bone formation and apposition than the native ECM protein coating, demonstrating the benefit of integrin-target mimetic peptides over whole biomolecules.

This work proposes a specific biomolecular strategy to improve bone regeneration and osseointegration by exploiting the cell adhesive activity of type I collagen, the most abundant matrix component in bone. In particular, type I collagen modulates intracellular signal transduction by binding to the $\alpha_2\beta_1$ integrin, which enhances the expression of the osteoblastic phenotype. It also exhibits low immunogenicity and high conformational stability, making it extremely suitable for implantation. However, designing surface treatments using whole matrix molecules, such as type I collagen, is often limited by a lack of specificity for particular integrins and thus exhibit minimal control over cellular responses. In addition, native matrix proteins often have binding sites for other ligands, which may trigger antagonistic signaling cascades that may ultimately interfere with desired cell functions. The GFOGER peptide (SEQ ID NO:1) strategy described in this study targets the $\alpha_2\beta_1$ integrin-ligand interaction that is crucial for the development and maintenance of the osteoblast phenotype as well as the mineralization of the extracellular matrix. In vitro assays using bone marrow stromal cells verified that a GFOGER peptide (SEQ ID NO:1) coating enhances expression of multiple osteoblast-specific genes and alkaline phosphatase activity when compared to untreated titanium controls. This bioactive treatment also improved calcification of the extracellular matrix, demonstrating functional osteoblastic differentiation. Notably, the cortical bone implantation studies revealed greater bone tissue formation on the surface of GFOGER peptide (SEQ ID NO:1)-treated titanium implants, in terms of both quantity and connectivity. Most significantly, it has been shown that the GFOGER peptide (SEQ ID NO:1) coating improved the implant's mechanical fixation and functional osseointegration as determined by a quantitative pull-out test. Faster integration of these GFOGER peptide (SEQ ID NO:1) coated implants would result in sooner and more reliable loading in a clinical setting, improving device function and patient outcomes. Not only does this bioactive coating enhance bone formation and implant integration, but it is also created using a single-step procedure conducted under physiological conditions, thus eliminating the cytotoxicity and biocompatibility concerns associated with covalent immobilization methods. As such, this GFOGER peptide (SEQ ID NO:1) surface treatment represents a simple, clinically relevant approach to improving orthopaedic and dental titanium implant integration. Due to the fundamental character of receptor-ligand principles and the significance of cell-collagen interactions in multiple tissues, this material coating strategy may also have the potential to improve implant integration in non-orthopaedic tissue systems. For example, this implant coating technology can be applied to cardiovascular, skin, liver, and kidney-related devices as the $\alpha_2\beta_1$ integrin plays a central role in the function and repair of these tissues.

Example 4

Recombinant $FNIII_{7-10}$ has Equivalent Biological Activity as Plasma FN

Figure 6A:
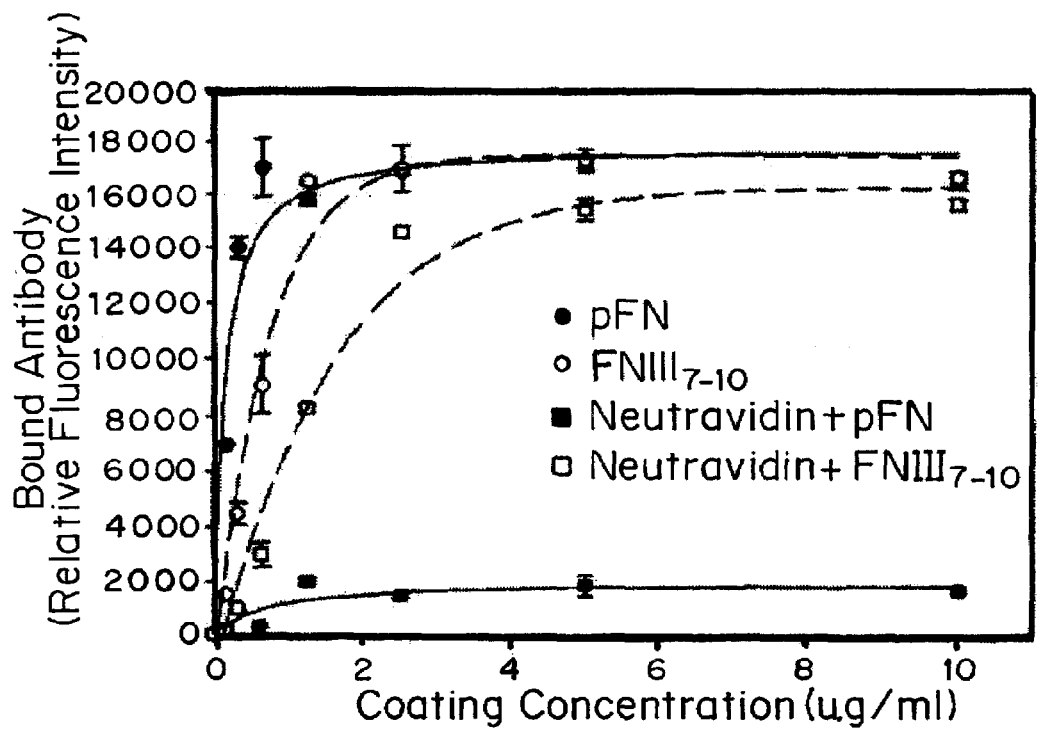
FIG. 6A is a line graph of the relative fluorescence intensity of bound antibody versus coating concentration (μg/ml) of passively adsorbed pFN and $FNIII_{7-10}$.
Figure 6B:
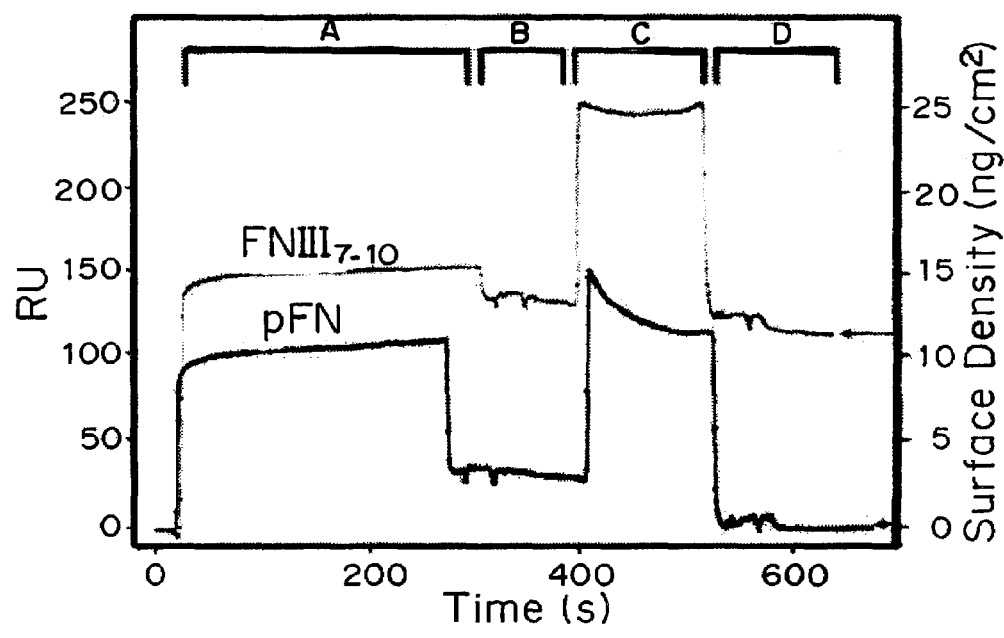
FIG. 6B shows SPR measurements on streptavidin-coated chips demonstrating successful biotinylation of $FNIII_{7-10}$. The y-axes are relative units and surface density ($ng/cm^2$).

A recombinant FN fragment ($FNIII_7$-10), presenting both the RGD and the synergy PHSRN (SEQ ID NO:11) domain in the correct native structure and orientation has previously been developed in order to target the $\alpha_5\beta_1$ Recombinant DNA technology allows for production of FN-mimetic ligands that reconstitute the secondary structure of the native ligand and affords the ability to engineer enhanced or new functionality. A monobiotinylated has been produced by encoding a biotinylation sequence at the amine terminus of the protein. This FN fragment represents an enhanced version of the previously described fragment with a single biotin tag introduced at a specific site. In addition to providing a simple system to generate large quantities of purified protein via affinity chromatography (2-10 mg from 1 L culture, >98% purity), this strategy incorporates a well-defined tag for tethering onto avidin supports as well as a tracking marker for future in vitro and in viva studies. The biological activity of $FNIII_{7-10}$ was evaluated ELISA using the HFN7.1 monoclonal antibody, which is specific for the central cell-binding domain in the 9-10$^{th}$ type III repeats of FN. Furthermore, it has been shown that HFN7.1 binding efficiency correlates closely with the binding affinity of the integrin $\alpha_5\beta_1$ for FN. For passively adsorbed ligands, HFN7.1 binding increased with protein coating concentration for both pFN and $FNIII_{7-10}$, and there were no significant differences in either the hyperbolic shape or magnitude for the binding curves (FIG. 6A), indicating equivalent functional activity between monobiotinylated $FNIII_{7-10}$ and pFN. To demonstrate biotinylation of the fragment, both ELISA on Neutravidin-coated polystyrene and SPR on streptavidin-coated gold chips (FIG. 6B) were performed. High levels of HFN7.1 antibody bound to $FNIII_{7-10}$ incubated on Neutravidin-coated surfaces, whereas background levels of HFN7.1 binding were observed on Neutravidin supports exposed to pFN (no biotin tag).

Similarly, SPR measurements revealed high levels of immobilized $FNIII_{7-10}$ on strepavidin-coated chips.

Example 5

$FNIII_{7-10}$ Displays Enhanced Cell Adhesive Activity Compared to RGD Peptides Mixed alkanethiol SAMs were used as model surfaces presenting well-defined anchoring groups (—COOH) for controlled tethering of ligands in a protein adsorption resistant background (tri(ethylene glycol groups): $EG_3$). Peptides were tethered via free amines using NHS/EDC coupling chemistry. $FNIII_{7-10}$ tethering/adsorption onto activated/unactivated SAMs with $EG_6$-COOH:$EG_3$ has been examined in solution ratios ranging from 0.0001 to 0.1 via ELISA (data not shown). An $EG_6$-COOH:$EG_3$ solution ratio of 0.02 was determined to yield the highest tethered ligand density while maintaining background levels of non-specific adsorption. This model system presents a well-defined surface with a single adhesive ligand that allows direct functional comparison on a molar basis among different adhesive ligands.

Figure 7:
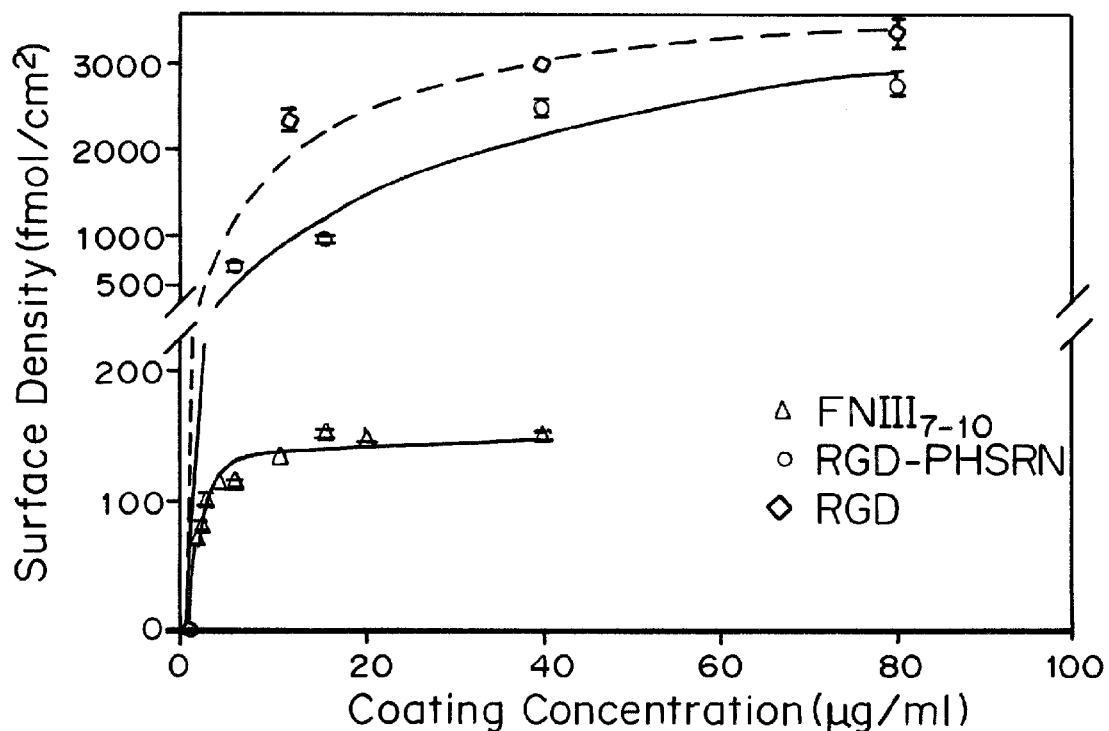
FIG. 7 is a line graph of surface density ($fmol/cm^2$) of RGD peptide (SEQ ID NO:3), and "RGD-PHSRN" ($GRGDG_{13}PHSRN$, SEQ ID NO:4) tethered to 2% $EG_6$-$COOH:EG_3$ SAM surfaces as a function of coating concentration (μg/ml) determined by surface plasmon resonance (SPR).

Three adhesive ligands were examined: (i) "RGD peptide" (GRGDSPC) (SEQ ID NO:3); (ii) "RGD-PHSRN peptide" (GRGDG$_{13}$PHSRN) (SEQ ID NO:4) presenting the RGD and PHSRN (SEQ ID NO:11) motifs joined by a polyglycine sequence designed to mimic the spacing of the domains in FN but not interfere with the adhesion characteristics of the two linked sequences; and (iii) $FNIII_{7-10}$. Quantification of ligand tethering onto SAMs was conducted via SPR. Tethered ligand surface density increased hyperbolically with coating concentration, reaching saturation levels at higher concentrations (FIG. 7). The measured surface densities are in good agreement with previous results, and are below the theoretical limits based on the calculated surface density of the $EG_6$-COOH thiols. Although these surfaces were prepared in situ in the SPR, as opposed to the surfaces prepared on the bench-top used for the cell culture work, ELISA-based measurements indicated no significant differences in tethered profile shape or relative densities (data not shown), supporting the validity of these quantitative density values. This data indicates that control over tethered peptide density can be achieved by varying coating concentration accordingly. Although the tethering curves exhibited similar hyperbolic profiles, RGD peptide (SEQ ID NO:3) and RGD-PHSRN (SEQ ID NO:4) tethered at >10-fold higher molar densities than $FNIII_{7-10}$ (FIG. 7). Tethering efficiencies for RGD peptide (SEQ ID NO:3) and RGD-PHSRN (SEQ ID NO:4) were identical. Tethered ligands were biologically active as determined by cell spreading. At saturated surface densities, all engineered surfaces exhibited equivalent levels of cell spreading, while very few cells attached to $EG_3$ or unactivated $EG_6$-COOH: $EG_3$ surfaces (data not shown).

Figure 8:
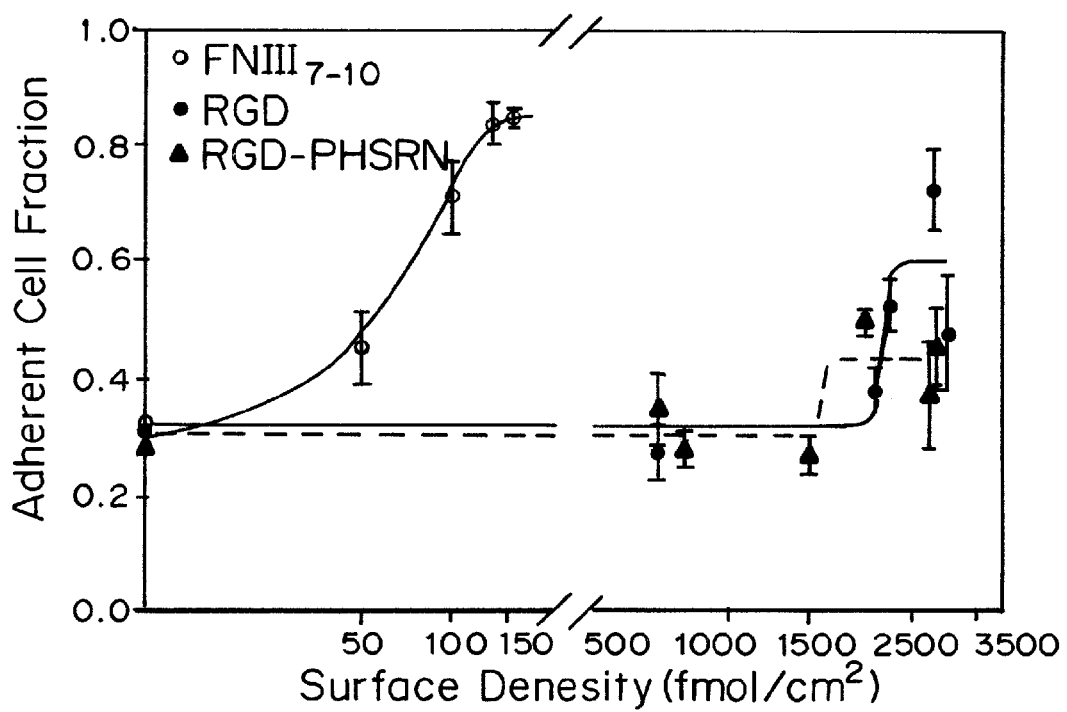
FIG. 8 is a line graph showing MC3T3-E1 cell adhesion fraction to SAMs presenting controlled densities of bioadhesive ligands RGD peptide (SEQ ID NO:3), or RGD-PHSRN (SEQ ID NO:4).

To further characterize the adhesive activities of these engineered biointerfaces, the adhesion strength of MC3T3-E1 cells was measured using a centrifugation assay that applies controlled detachment forces to adherent cells. For all surfaces, the fraction of adherent cells increased sigmoidally with adhesive ligand surface density (FIG. 8), and adhesion strength was characterized as the ligand density required for half-maximal adhesion ($ADH_{50}$). Adhesion strength is inversely related to $ADH_{50}$, as a shift of the curve left (decreasing $ADH_{50}$) represents an increase in adhesion strength since less ligand is needed for cell adhesion. Cell adhesion profiles for RGD peptide (SEQ ID NO:3) and RGD-PHSRN-tethered (SEQ ID NO:4) surfaces were almost identical, and $ADH_{50}$ values were 2300 and 1950 fmol/cm$^2$, respectively, indicating similar adhesive activity for these two peptides (FIG. 8). $FNIII_{7-10}$-tethered surfaces displayed a pronounced leftward shifted adhesion profile compared to the other two peptide tethered-surfaces, reflected in the relatively low $ADH_{50}$ value of 70 fmol/cm$^2$ (FIG. 8). These data indicate that the $FNIII_{7-10}$ tethered surface displays higher cell adhesive activity compared to RGD peptide (SEQ ID NO:3) or RGD-PHSRN (SEQ ID NO:4)-tethered surfaces.

Example 6

Figure 9A:
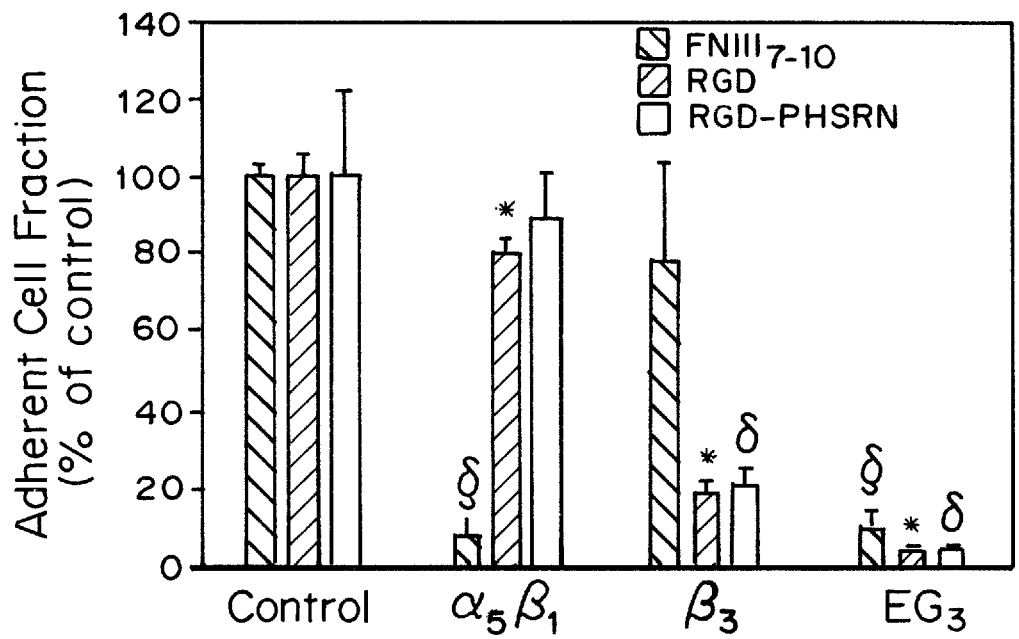
FIG. 9A is a panel of bar graphs showing adherent cell fraction on surfaces coated with $FNIII_{7-10}$, RGD peptide (SEQ ID NO:3), or RGD-PHSRN (SEQ ID NO:4). Surfaces presenting $FNIII_{7-10}$ display integrin biding specificity compared to RGD supports.

$FNIII_{7-10}$ Surfaces Display Different Integrin Specificity than RGD-Functionalized Supports These different adhesive surfaces were examined to determine if they supported cell adhesion by binding different integrin receptors. Function-perturbing antibodies directed against different integrin subunits were used to block adhesion to the engineered interfaces. Since integrins $\alpha_5\beta_1$ and $\alpha_v\beta_3$ represent the dominant adhesion receptors for FN in MC3T3-E1 cells, the contributions of these receptors to adhesion strength on the peptide-functionalized SAMs was examined. Surfaces were tethered with maximum density of ligand, and the relative cell adhesion was normalized to unblocked controls. Blocking antibodies directed against $\alpha_5\beta_1$ integrin reduced adhesion to background levels ($EG_3$) for the $FNIII_{7-10}$ tethered surface, but only slightly reduced adhesion on the RGD peptide (SEQ ID NO:3) and RGD-PHSRN (SEQ ID NO:4) surfaces (FIG. 9A). In contrast, antibodies against the $\beta_3$ integrin subunit did not alter adhesion significantly for $FNIII_{7-10}$-tethered surfaces, but reduced adhesion over 75% for both the RGD peptide (SEQ ID NO:3) and RGD-PHSRN (SEQ ID NO:4) surfaces (FIG. 9A). These results demonstrate that the $FNIII_{7-10}$-tethered surface primarily supports $\alpha_5\beta_1$-mediated adhesion; whereas, the RGD peptide (SEQ ID NO:3)- and RGD-PHSRN (SEQ ID NO:4)-functionalized surfaces promote $\alpha_v\beta_3$-mediated cell adhesion.

Since MC3T3-E1 cells assemble robust focal adhesions containing clustered integrins and intracellular structural and signaling proteins, integrin binding and focal adhesion assembly on the engineered interfaces was examined by staining for different integrin subunits and vinculin, which localizes to focal adhesions. MC3T3-E1 cells were allowed to adhere on each saturated ligand-functionalized support for 4 h and integrin binding was evaluated via a crosslinking/extraction and immunostaining protocol, which isolates integrins ligated to the ligand. Cells adhering to $FNIII_{7-10}$-tethered surfaces displayed robust, well-defined adhesive structures containing $\alpha_5\beta_1$ integrins but minimal $\alpha_v\beta_3$ binding. Cells on RGD-tethered surfaces exhibited clustering of $\alpha_v\beta_3$ and little staining for $\alpha_5\beta_1$. The crosslinking and extraction technique relies in coupling free amines on both the receptor and ligand. Since the tethered RGD has no free amine, the $\alpha_v\beta_3$ staining in the RGD surfaces is attributed to focal adhesions that were not completely extracted. These results are further supported by the integrin antibody blocking adhesion data. Both surfaces assembled focal adhesions containing vinculin. These results further demonstrate that surfaces presenting $FNIII_{7-10}$ primarily support $\alpha5\beta_1$-mediated adhesion, while RGD functionalized SAMs mediate adhesion via $\alpha_v\beta_3$.

Example 7

Figure 9B:
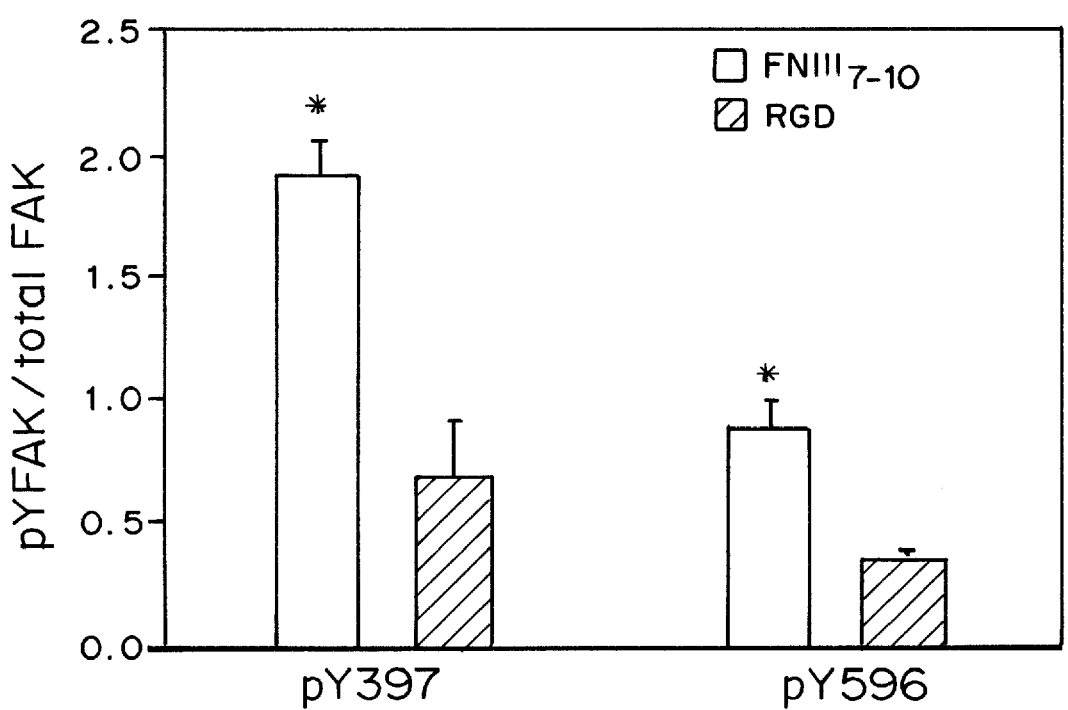
FIG. 9B is a bar graph of FAK kinase activation (pY-FAK/total FAK) in cells interacting with $FNIII_{7-10}$-tethered surfaces compared to the RGD-functionalized supports using antibodies pY397 or pY576.
Figure 10:
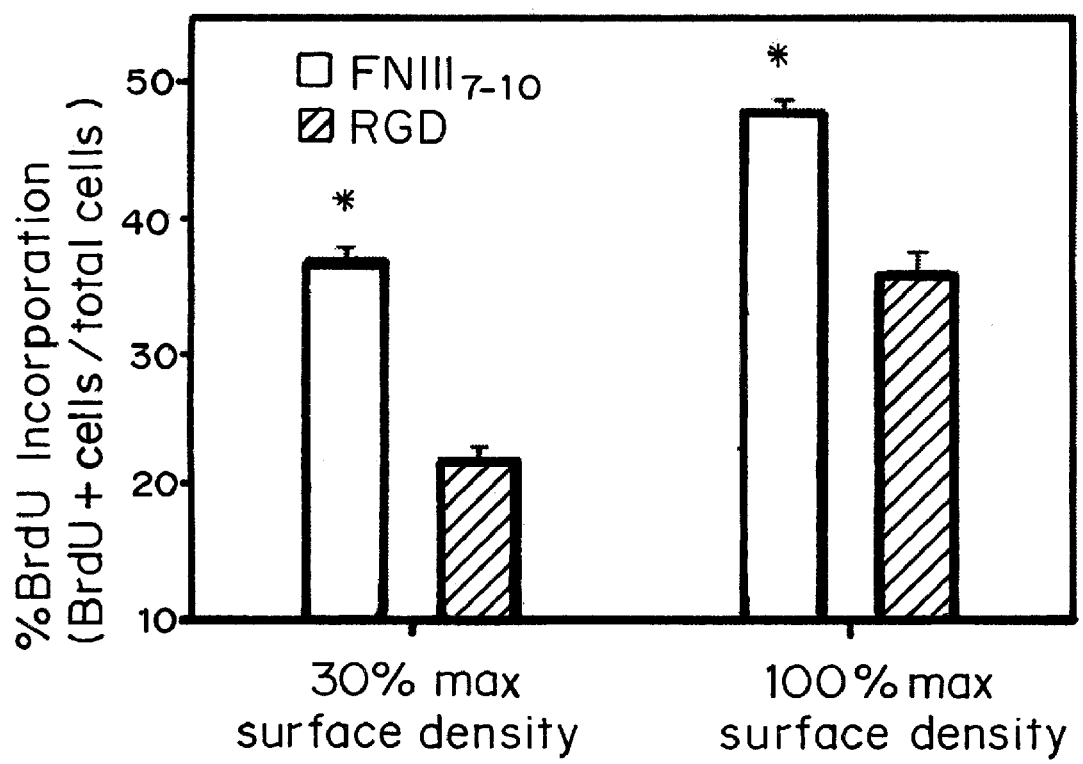
FIG. 10 is a bar graph showing percent BrdU incorporation (BrdU+ cells/total cells) for MC3T3-E1 cells cultured for 20 h on ROD peptide (SEQ ID NO:3) and $FNIII_{7-10}$ tethered surfaces for two different peptide surface densities.

$FNIII_{7-10}$ Interfaces Trigger Enhanced Signaling and Cell Proliferation Compared to RGD Surfaces The bioadhesive interfaces were examined to determine whether they modulate intracellular signaling and high-order cell activities. Levels of FAK phosphorylation as a marker of integrin-mediated signaling were examined. FAK localizes to focal adhesions and activates various signaling cascades regulating cell survival, proliferation and differentiation. Phosphorylation of important tyrosine residues was probed for using site-specific antibodies in Western blotting. Phosphorylation of tyrosine-397, the autophosphorylation site on FAK which also binds to the p85 subunit of PI3-kinase, was increased almost threefold on the $FNIII_{7-10}$ surface compared to the RGD-tethered surface at maximum peptide densities. Similarly, phosphorylation of tyrosine-576, located in the FAK catalytic loop and responsible for maximal FAK kinase activity, was significantly higher on the $FNIII_{7-10}$-tethered surface compared to the ROD-functionalized support (FIG. 9B). The tyrosine-861, a major Step phosphorylation site, was phosphorylated at similar levels among both peptide-tethered surfaces (data not shown). These results demonstrate differential activation of FAK on these engineered interfaces, suggesting that different integrins trigger different signaling pathways on biomimetic surfaces. Because integrin-mediated activation of FAK has been linked to upregulation of cell proliferation, adhesion to the different biointerfaces was examined to determine if it would modulate MC3T3-E1 proliferation. The proliferation rate of cells seeded for 16 h on each ligand-tethered surface was probed by BrdU incorporation. Cells seeded on $FNIII_{7-10}$-functionalized surfaces displayed a two-fold increase in cell proliferation rate compared to ROD-tethered surfaces at low and high relative peptide surface densities (FIG. 10).

Well-defined biointerfaces are provided that present different adhesive ligands to directly compare their biological activities in terms of cell adhesion strength, integrin binding, and signaling. Mixed SAMs of $COOHEG_6$- and $EG_3$-terminated alkanethiols were optimized to engineer robust supports that present anchoring groups for ligand tethering within a non-fouling, protein adsorption-resistant background. Controlled bioadhesive interfaces were generated by tethering adhesive ligands via standard NHS/EDC chemistry, and the resulting tethered surface density could be easily modulated by altering the ligand concentration in solution during tethering. The ability to precisely control tethered ligand densities is an important design parameter as cell adhesion, focal adhesion assembly, spreading and migration, neurite extension, and cell differentiation exhibit peptide density-dependent effects. The adhesive activities of three FN-mimetic ligands of increasing complexity were examined: (i) linear RGD peptide (SEQ ID NO:3) presenting the minimal cell adhesive motif of FN; (ii) RGD-PHSRN peptide (SEQ ID NO:4) presenting the RGD and PHSRN (SEQ ID NO:11) motifs joined by a polyglycine sequence designed to mimic the spacing of these domains in FN, and (iii) recombinant $FNIII_{7-10}$ reconstituting the primary and secondary structure of the central cell binding domain of FN. A linear RGD peptide (SEQ ID NO:3) was used in this study. Furthermore, current biomimetic surfaces mainly focus on linear RGD, making the use of linear RGD in this study more relevant to current strategies. On a molar basis, biointerfaces presenting $FNIII_{7-10}$ exhibited significantly higher adhesion strength, FAK activation, and cell proliferation rate than supports presenting RGD peptide (SEQ ID NO:3) or RGD-PHSRN (SEQ ID NO:4). Moreover, $FNIII_{7-10}$-functionalized surfaces displayed specificity for $\alpha_5\beta_1$ integrin, while cell adhesion to SAMs presenting RGD peptide (SEQ ID NO:3) or RGD-PHSRN (SEQ ID NO:4) was primarily mediated by $\alpha_v\beta_3$ integrin. These results are significant to the rational engineering of bioactive materials that promote cell adhesion and function. Importantly, recent evidence indicates that integrin binding specificity, particularly $\alpha_5\beta_1$ vs. $\alpha_v\beta_3$ regulates osteoblast and myoblast differentiation in response to biomaterial surface chemistry. Therefore, biomolecular engineering strategies that convey integrin binding specificity to bio-inspired materials may provide a facile route to elicit desired cellular responses. Finally, DNA recombinant technology provides a versatile platform to engineer bioactive ligands mimicking the structure of the native ligand as well as a system to incorporate new functionality.

The improved adhesive activities of $FNIII_{7-10}$-engineered surfaces compared to RGD peptide (SEQ ID NO:3)- and RGD-PHSRN (SEQ ID NO:4) functionalized supports can be attributed to enhanced binding of integrin $\alpha_5\beta_1$. Simple RGD linear peptides, even those co-presenting the PHSRN (SEQ ID NO:11) motif in the appropriate spacing as in the native FN molecule, cannot support binding of integrin $\alpha_5\beta_1$, but instead promote binding of $\alpha_V\beta_3$. The integrin specificity for $\alpha_5\beta_1$ of FNIII$_{7-10}$-tethered surfaces is attributed to the presentation of PHSRN (SEQ ID NO:11) and RGD in the same structural context as the native FN ligand, while the RGD peptides either lack the PHSRN (SEQ ID NO:11) site (RGD peptide, SEQ ID NO:3) or present it in a suboptimal orientation (RGD-PHSRN, SEQ ID NO:4). This result underscores the exquisite sensitivity of the integrin $\alpha_5\beta_1$-FN interaction on the specific molecular structure of the ligand. Notably, in addition to presenting PHSRN (SEQ ID NO:11) and RGD in a specific structural conformation, FNIII$_{7-10}$ has the RGD motif constrained to a loop extending from the backbone of the molecule. While this RGD constrained conformation probably improves receptor binding affinity, the improved specificity of FNIII$_{7-10}$ for $\alpha_5\beta_1$ integrin cannot be attributed to the constrained RGD loop. The $\alpha_5\beta_1$-mediated enhancements in adhesion strength, FAK activation, and cell proliferation rate on FNIII$_7$-10-engineered interfaces may reflect increases in the number of integrin-ligand bonds and/or $\alpha_5\beta_1$-specific activities.

Surfaces presenting RGD-PHSRN (SEQ ID NO:4) exhibited identical adhesive activities as RGD-functionalized supports, suggesting that the PHSRN (SEQ ID NO:11) motif in this peptide provides no additional effects. This result contrasts a previous study from Benoit and Anseth reporting enhanced activities of RGD-PHSRN (SEQ ID NO:4) compared to RGD peptide (SEQ ID NO:3) when presented within a hydrogel, although no antibody blocking experiments were performed. Possible explanations for this discrepancy include differences in peptide presentation/accessibility and cell type-specific activities. Furthermore, previous analyses with simple RGD peptide (SEQ ID NO:3) and PHSRN (SEQ ID NO:11) peptide mixtures also documented increases in cell adhesion compared to pure RGD. It is important to point out that two of these studies employed peptide-amphiphile supports, which exhibit significant peptide mobility. Reconfiguration of the interface may allow for rearrangement of ligands to approximate the structural context in FN and "fit" the integrin. Moreover, these studies used extremely high surface densities of peptides (compared to physiological densities of FN) that could give rise to nonphysiological effects. Comprehensive analyses, including antibody blocking, varying peptide surface densities, and signaling evaluations, are necessary to fully establish the adhesive activities of these engineered surfaces.

These data provide an experimental platform to engineer integrin-specific biointerfaces to manipulate cell and host responses to biotechnological/biomedical supports and implanted devices. Integrin binding specificity ($\alpha_5\beta_1$ vs. $\alpha_V\beta_3$) may regulate cellular activities, including cell cycle progression and expression of differentiated phenotypes, as well as tissue healing responses. This approach of conveying integrin binding specificity may provide a robust biomolecular strategy to elicit directed biological responses. In addition, integrin specific biomimetic surfaces utilizing recombinant peptides of matrix molecules, such as FNIII$_{7-10}$, often exhibit lower immunogenicity and higher stability than the whole proteins, as well as lack binding sites for other ligands which may impede in a more directed cellular response. In particular, this surface strategy may present a clinically relevant approach to improving bone formation and integration in biomedical devices and tissue-engineered scaffolds.

Example 8

Passively Adsorbed FNIII$_{7-10}$ Promotes Implant Osseointegration

Figure 11A:
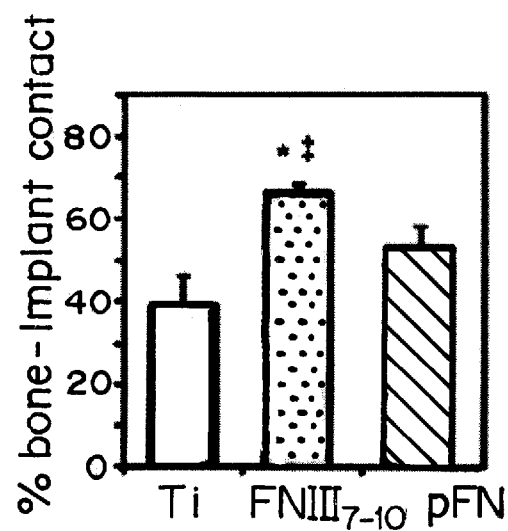
FIG. 11A is a bar graph showing percent bone implant contact on surfaces coated with $FNIII_{7-10}$, plasma fibronectin (pFN), or Ti surfaces.
Figure 11B:
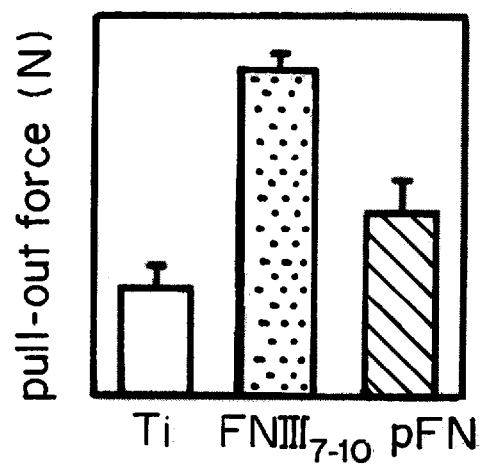
FIG. 11B is bar graph showing pull-out force (N) for implants coated with $FNIII_{7-10}$, pFN, or Ti surfaces

The ability of implant surfaces passively coated with FNIII$_{7-10}$ to promote bone formation in vivo and implant osseointegration was investigated. Titanium implants were coated with either FNIII$_{7-10}$ or plasma fibronectin (pFN) by incubating in 20 μg/ml solutions of the corresponding protein in PBS. Unmodified or protein-coated implants were implanted in the rat tibia as described above. After 4 weeks, implants were harvested and evaluated for bone-implant contact and osseointegration. FNIII$_{7-10}$-coated implants enhanced bone-implant apposition compared to unmodified titanium or implants coated with the native ligand pFN (FIG. 11A). More importantly, FNIII$_{7-10}$-coated implants significantly increased mechanical fixation 3-fold compared to unmodified and pFN-coated titanium (FIG. 11B). These results demonstrate that simple presentation of FNIII$_{7-10}$ on implant surfaces enhances bone formation and osseointegration compared to the current clinical standard (titanium) or implants coated with the native ligand pFN. The improved activity of FNIII$_{7-10}$ compared to pFN is attributed to the isolation of the bioactive, integrin-binding site of FN while excluding other domains that may have antagonistic effects.

Example 9

Functionalized Titanium with Poly(OEGMA) Brushes

Figure 12A:
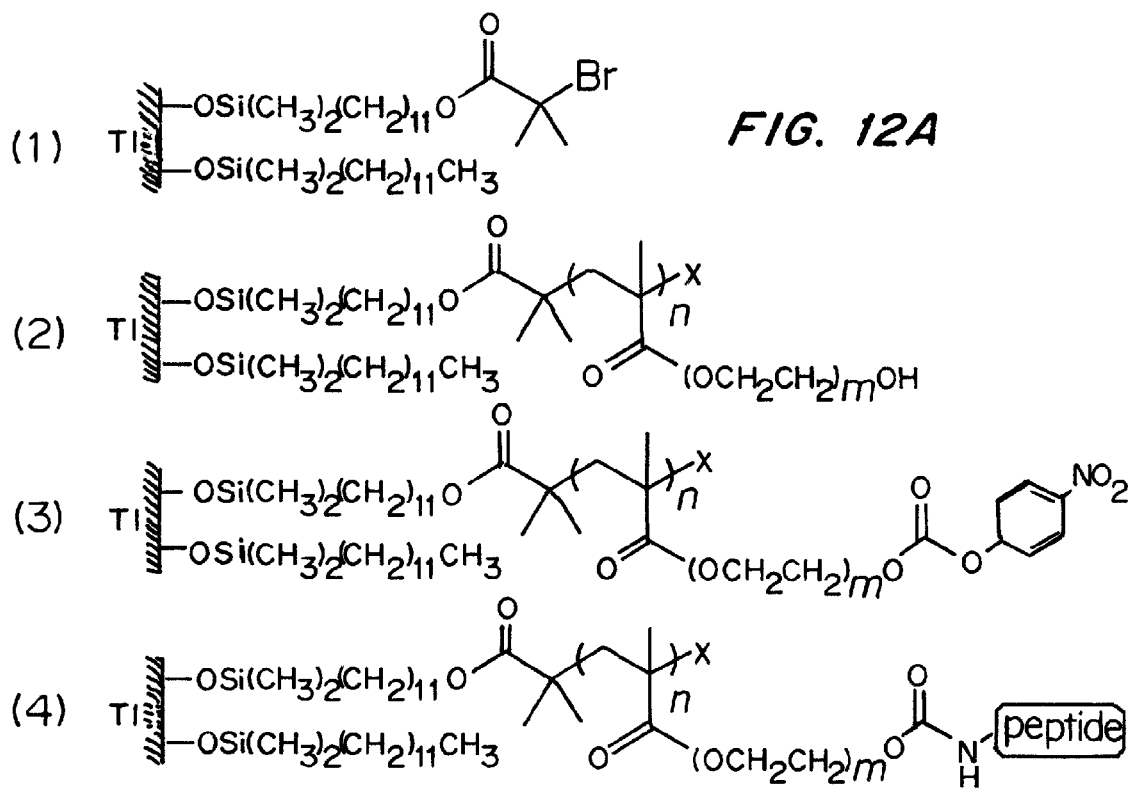
FIG. 12A shows the steps in tethering a peptide ligand to a surface of a device. (1) monolayer of silane initiator; (2) SI-ATRP of poly(OEGMA) brushes; (3) functionalization of OH groups with 4-nitrophenyl chloroformate; and (4) peptide tethering.
Figure 12B:
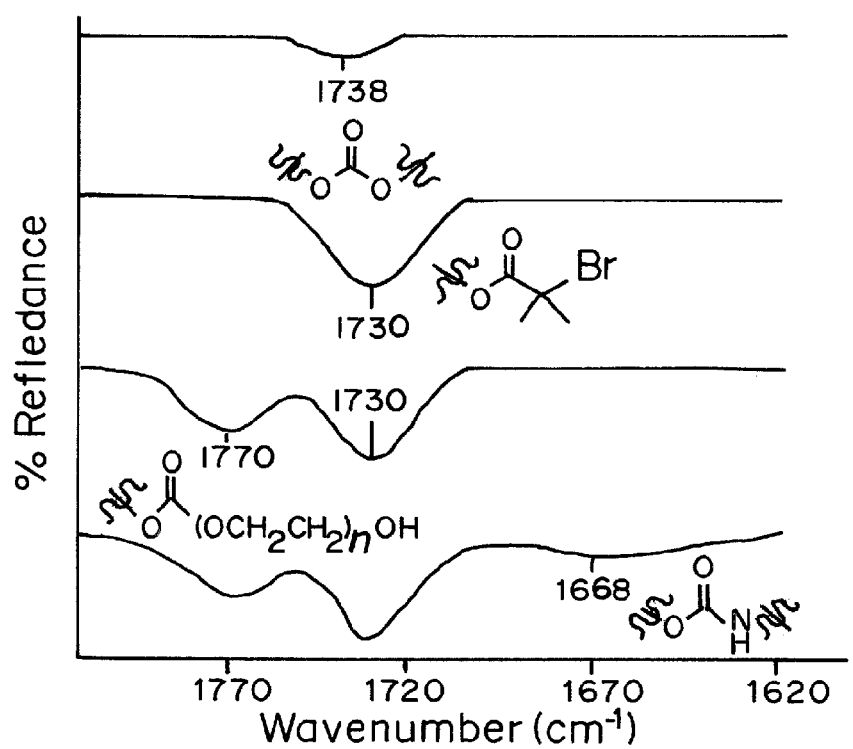
FIG. 12B presents FITR spectra of the steps in FIG. 12A: (1) monolayer of silane initiator (ester C=O, 1738 $cm^{-1}$) [presence of bromine was demonstrated by XPS (not shown)]; (2) SI-ATRP of poly(OEGMA) brushes (polymethacrylate C=O, 1730 $cm^{-1}$); (3) functionalization of OH groups with 4-nitrophenyl chloroformate (carbonate C=O, 1770 $cm^{-1}$); and (4) peptide tethering (amide C=O, 1670 $cm^{-1}$).

A "grafting from" approach using surface-initiated atom-transfer radical polymerization (SI-ATRP) of poly[oligo(ethylene glycol) methacrylate] (poly(OEGMA)) brushes on titanium (16) (FIG. 12A). Briefly, a 1:1 mixed self-assembled monolayer (SAM) of bromine-terminated initiator and unreactive, methyl-terminated co-adsorbate was formed on a clean titanium surface. The terminal bromine served as the radical initiator for the subsequent SI-ATRP of oligo(ethylene glycol) monomer to form thick, dense poly(OEGMA) brushes. The hydroxyl groups at the termini of the oligo (ethylene glycol) side chains of poly(OEGMA) were converted to 4-nitrophenyl carbonate by treatment with 4-nitrophenyl chloroformate (NPC) and functionalized with bioadhesive ligands via a urethane linkage. The progress of the synthesis was monitored by X-ray photoelectron spectroscopy (XPS) and glancing angle Fourier transform infrared (FTIR) spectroscopy (FIGS. 12A, 12B).

Figure 12C:
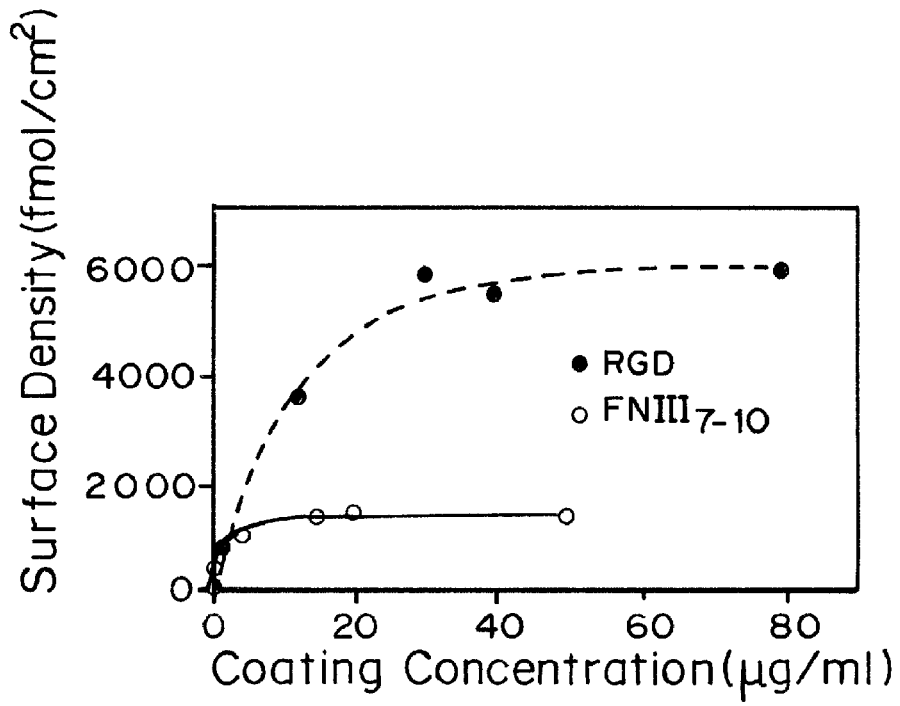
FIG. 12C is a line graph of tethered densities of RGD peptide (SEQ ID NO:3) and $FNIII_{7-10}$ ($fmol/cm^2$) versus coating concentration (μg/ml) of RGD peptide (SEQ ID NO:3) or $FNIII_{7-10}$. (hyperbolic curve fit, $R^2$=0.95).

Two bioadhesive ligands with different integrin specificities were examined: (i) the recombinant fragment FNIII$_{7-10}$, which presents the RGD motif in the 10$^{th}$ type III repeat and the PHSRN (SEQ ID NO:11) synergy sequence in the 9$^{th}$ type III repeat of FN in the correct structural context and exhibits high selectivity for integrin $\alpha_5\beta_1$, and (ii) a linear RGD oligopeptide (GRGDSPC) (SEQ ID NO:3) that primarily supports $\alpha_V\beta_3$-mediated adhesion and is considered the "gold" standard in the field. Controlled surface densities of tethered ligands were obtained by treating the NPC-modified polymer brushes with varying concentrations of peptide (FIG. 12C). The differences in tethering efficiency between FNIII$_{7-10}$ and RGD peptide (SEQ ID NO:3) can be attributed to significant differences in ligand size. Importantly, ligand densities adsorbed on control surfaces presenting unmodified poly (OEGMA) brushes were <5% of the density immobilized on the functionalized surfaces, demonstrating the non-fouling nature of the unmodified poly(OEGMA) brush.

Example 10

Assessment of In Vitro Bioresistance and Adhesive Capacity

Figure 12D:
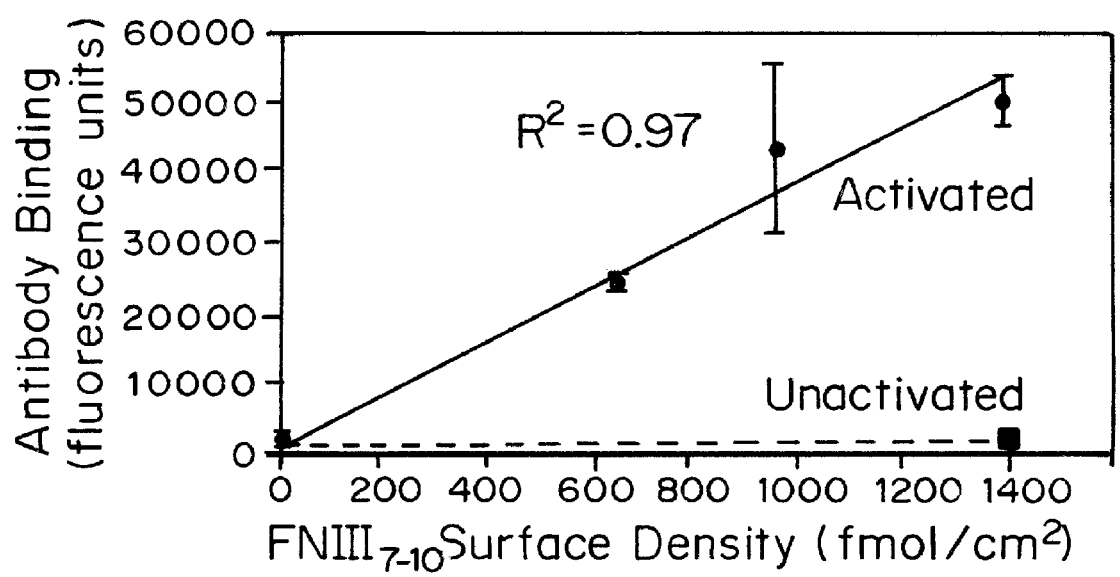
FIG. 12D is a line graph of antibody binding (fluorescence units) versus $FNIII_{7-10}$ surface density ($fmol/cm^2$). $FNIII_{7-10}$ activity was detected on the NPC-modified poly(OEGMA) brushes (but not the unmodified brushes).

The in vitro bioresistance and adhesive capacity of unmodified poly(OEGMA) brushes and brushes with peptide tethered on titanium were assessed. Surfaces were incubated in serum-containing media for various times and subsequently challenged with osteoblastic cells for 1 h. In contrast to control unmodified titanium which supported high levels of cell adhesion and spreading, unmodified poly(OEGMA) brushes resisted cell adhesion for over 56 days. The unfunctionalized poly(OEGMA) brushes exhibited excellent bioresistance compared to commonly-used self-assembled monolayers of tri(ethylene glycol)-functionalized alkanethiols on gold, which displayed loss of bioresistance by the day time point in serum-containing media. Moreover, poly(OEGMA) brushes presenting either $FNIII_{7-10}$ or RGD supported levels of cell adhesion comparable to the unmodified titanium, demonstrating that the tethered ligand is in a bioactive form that supports adhesive activities. Surface density dependent increases in available $FNIII_{7-10}$ ligand was demonstrated using a receptor-mimetic antibody-based assay (FIG. 12D). Taken together, these results demonstrate a robust approach to coat clinical-grade titanium with non-fouling/bioresistant oligo(ethylene glycol)-substituted polymer brushes which can be functionalized with controlled densities of bioadhesive ligands.

Example 11

In Vitro Evaluation of Engineered Titanium Surfaces

Figure 13A:
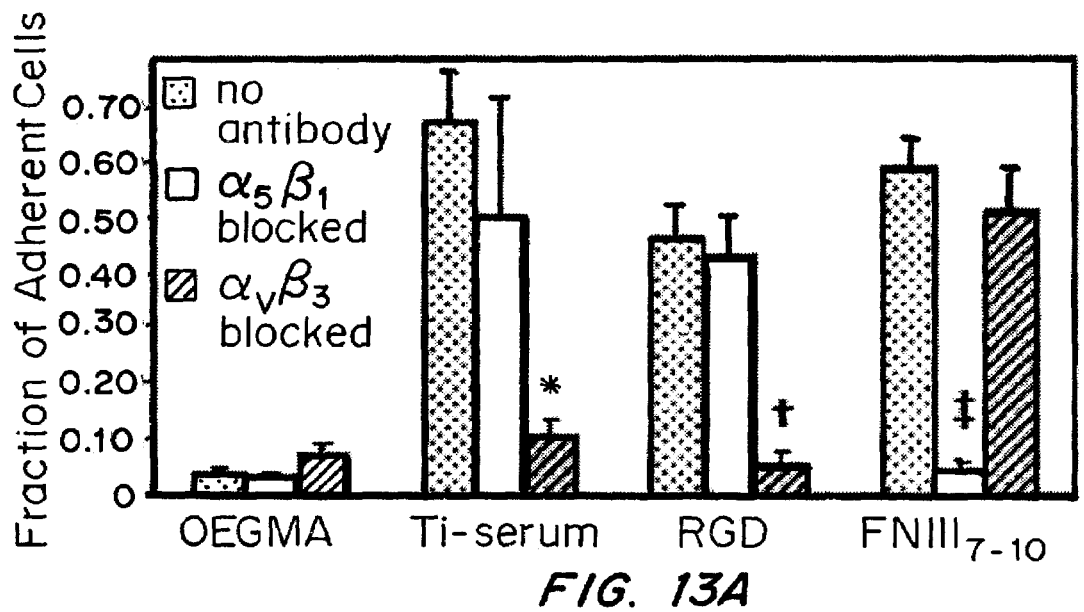
FIG. 13A is a panel of bar graphs showing fraction of bone marrow stromal cell adhesion to engineered surfaces mediated by integrin receptors as demonstrated by blocking antibodies against integrin subunits alpha5 or alphaV. Ti-serum surface: * vs. no antibody control (p<0.01); RGD tethered surface: † vs. no antibody control (p<0.01); $FNIII_{7-10}$ tethered surface: ‡ vs. no antibody control (p<0.005).
Figure 13B:
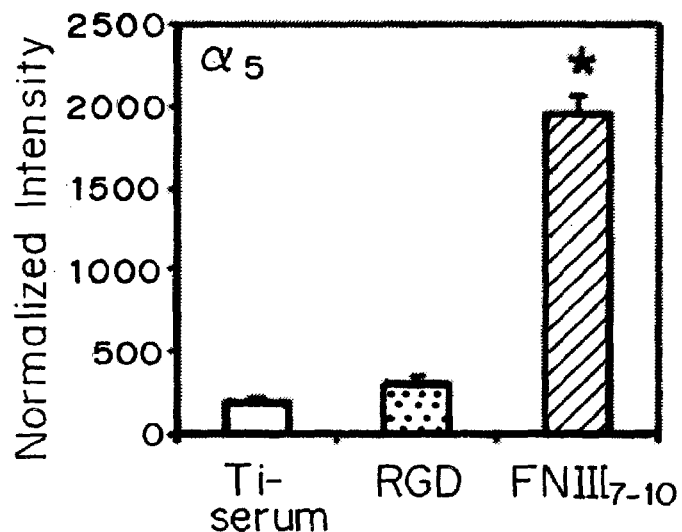
FIG. 13B is a bar graph showing normalized intensity due to binding of alpha5beta1 integrin to $FNIII_{7-10}$ tethered brushes; RGD tethered brushes; or Ti support (p<0.01) using a crosslinking/extraction/reversal procedure for stromal cells plated on ligand-tethered brush surfaces of equimolar density.

In vitro evaluation of these engineered titanium surfaces was performed using primary rat bone marrow stromal cells since this heterogeneous population contains osteoprogenitors, and human bone marrow stromal cells are currently used in clinical applications. Cell adhesion was examined using a centrifugation assay that applies a controlled detachment force. To allow direct comparisons between ligand-tethered surfaces, an equimolar ligand density of 0.9 µmol/cm² was used; this value represents the highest ligand density that could be ascribed for both surfaces to be equimolar. Upon exposure to serum, high levels of cell adhesion were observed for polymer brushes modified with either $FNIII_{7-10}$ or RGD brushes, as well as unmodified titanium (which adsorbs RGD-containing adhesive proteins from serum) (FIG. 13A). Unmodified poly(OEGMA) brushes displayed background levels of adhesion, further illustrating the bioresistance of this system. Importantly, a blocking anti-$\alpha_5$ antibody completely eliminated cell adhesion to $FNIII_{7-10}$-tethered surfaces (p<0.005), whereas an anti-$\alpha_v$ antibody had no effect, verifying the specificity of this surface for $\alpha_5\beta_1$ integrin. Conversely, a function-perturbing anti-$\alpha_v$ antibody eliminated adhesion to both ROD-tethered surfaces and serum-exposed unmodified titanium (p<0.01) (FIG. 13A), indicating that adhesion to these surfaces is primarily mediated by the $\alpha_v\beta_3$ integrin. As a complementary test of integrin specificity, integrin binding was quantified using a biochemical cross-linking/extraction/reversal technique. Consistent with the antibody blocking experiments, $FNIII_{7-10}$-tethered brushes supported significantly higher levels of bound $\alpha_5\beta_1$ integrin compared to RGD-tethered brushes and serum-exposed titanium (p<0.01) (FIG. 13B). On the other hand, the RGD-tethered brushes and serum-exposed titanium supported higher levels of bound $\alpha_v\beta_3$ that the $FNIII_{7-10}$ support (p<0.006). These data demonstrate that $FNIII_{7-10}$-functionalized titanium selectively supports $\alpha_5\beta_1$-mediated cell adhesion, whereas the RGD-tethered surface primarily binds $\alpha_v\beta_3$ integrin.

Example 12

FAK Phosphorylation Assessment of Engineered Surfaces

Figure 13C:
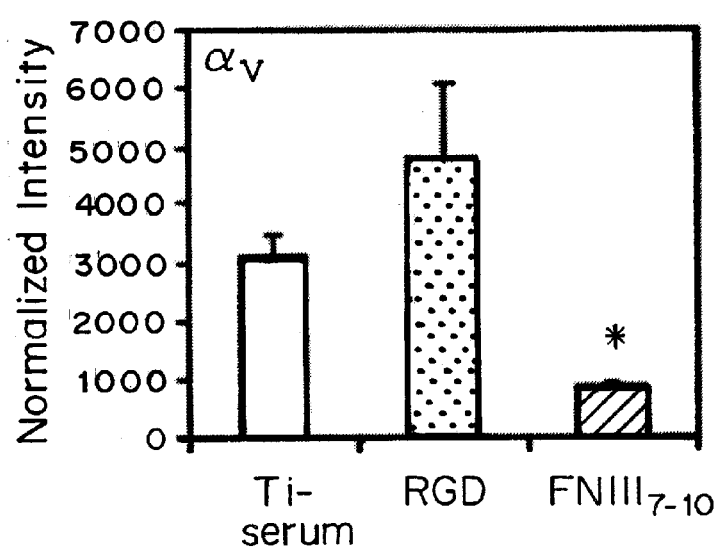
FIG. 13C is a bar graph showing normalized intensity due to binding of alphaV integrin to $FNIII_{7-10}$ tethered brushes (p<0.006), RGD tethered brushes, or Ti support using a crosslinking/extraction/reversal procedure for stromal cells plated on ligand-tethered brush surfaces of equimolar density.
Figure 13D:
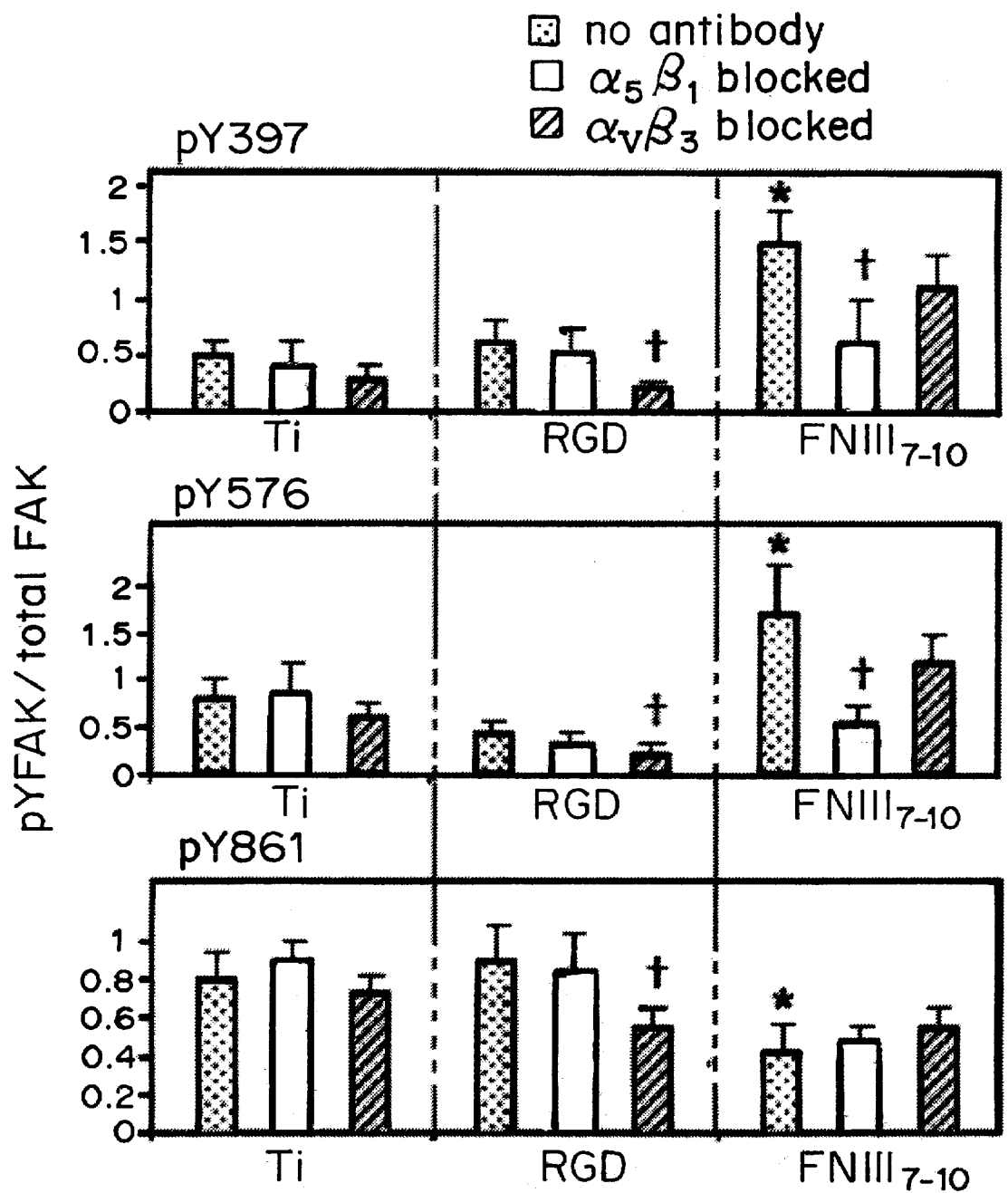
FIG. 13D is a panel of bar graph of FAK activation on equimolar ligand-tethered brush surfaces and serum-treated titanium. Relative levels of phospho-Y in FAK in the presence or absence of integrin blocking antibodies are shown. Activation levels for Y397 and Y576 were higher on $FNIII_{7-10}$-tethered brushes than RGD-functionalized and Ti-serum supports (p<0.01). Y861 phosphorylation levels were reduced in $FNIII_{7-10}$-functionalized titanium relative to the other surfaces (p<0.03). Integrin blocking antibodies selectively reduced FAK phosphorylation. Y397: † vs. no antibody control (p<0.04); Y576: † vs. no antibody control (p<0.05); Y861: † vs. no antibody control (p<0.05).

As a final demonstration of the integrin-specific nature of these engineered supports, FAK phosphorylation was assessed in the presence of integrin blocking antibodies. FAK is an intracellular signaling molecule involved in integrin-mediated signal transduction and the osteogenic differentiation pathway. Phosphotyrosine-specific antibodies were used to examine the activation state of three important tyrosines in FAK: Y397 (autophosphorylation site), Y576 (essential for maximal kinase activity), and Y861 (major Src phosphorylation site) (FIG. 13C). FAK Y397 and Y576 exhibited higher phosphorylation levels on $FNIII_{7-10}$-engineered surfaces compared to RGD-functionalized brushes and serum-exposed titanium (p<0.01), whereas Y861 phosphorylation was elevated for the RGD-functionalized and serum-exposed titanium relative to the FNIII7-10-tethered surface (p<0.03). Moreover, blocking antibodies against α5, but not β3, reduced the levels of phospho-Y397 and Y576 on the $FNIII_{7-10}$-presenting titanium (p<0.04). For the RGD-functionalized poly(OEGMA) brushes, only the anti-$\beta_3$ antibody reduced FAK phosphorylation (p<0.05). These differences in integrin binding specificity and FAK activation modulate cell signaling pathways and higher order cellular activities.

Example 13

Assessment of Osteoblastic Gene Expression of Engineered Surfaces

Figure 14A:
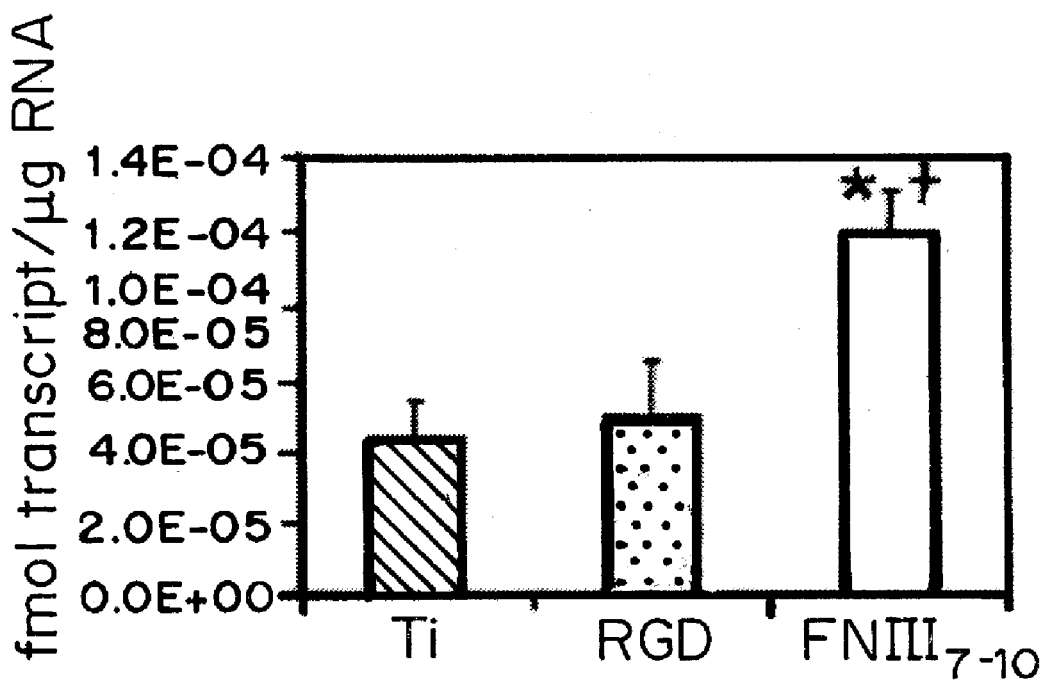
FIG. 14A is a bar graph showing gene expression levels for Runx2 on Ti, RGD-tethered or $FNIII_{7-10}$-tethered surfaces.
Figure 14B:
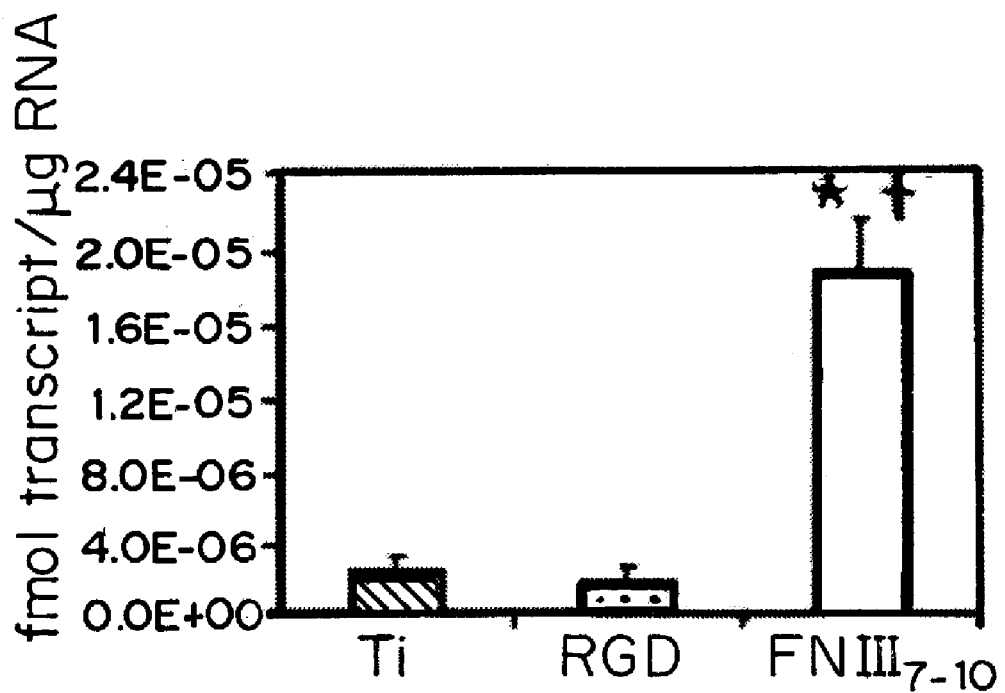
FIG. 14B is a bar graph showing gene expression levels for osteocalcin on Ti, RGD-tethered or $FNIII_{7-10}$-tethered surfaces.
Figure 14C:
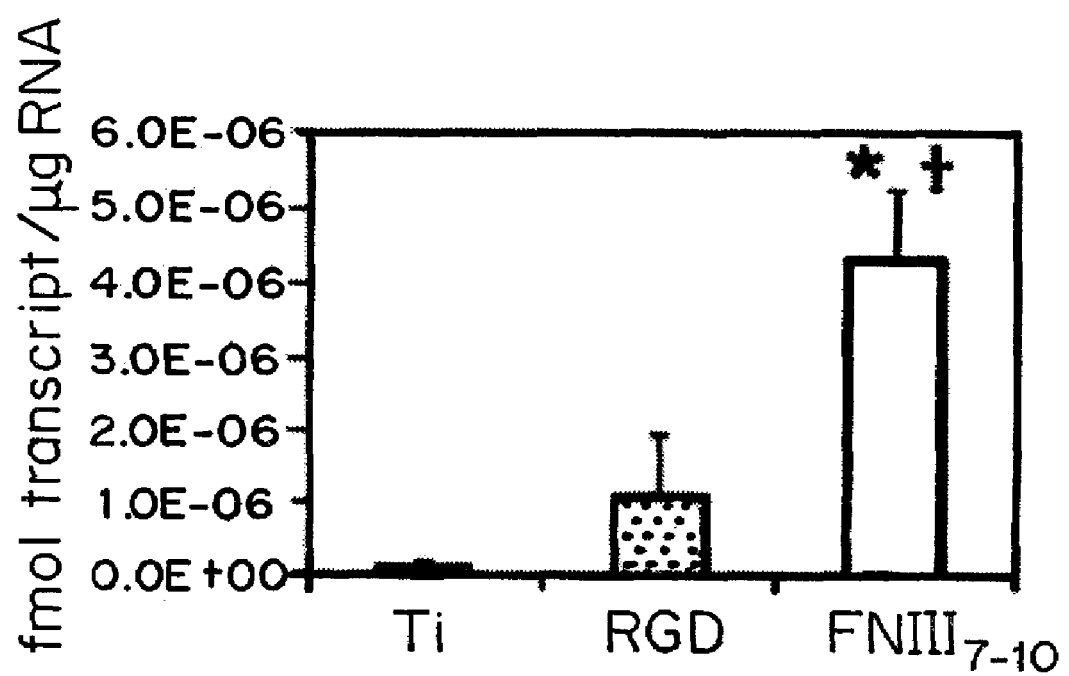
FIG. 14C is a bar graph showing gene expression levels for bone sialprotien on Ti, RGD-tethered or $FNIII_{7-10}$-tethered surfaces.
Figure 14D:
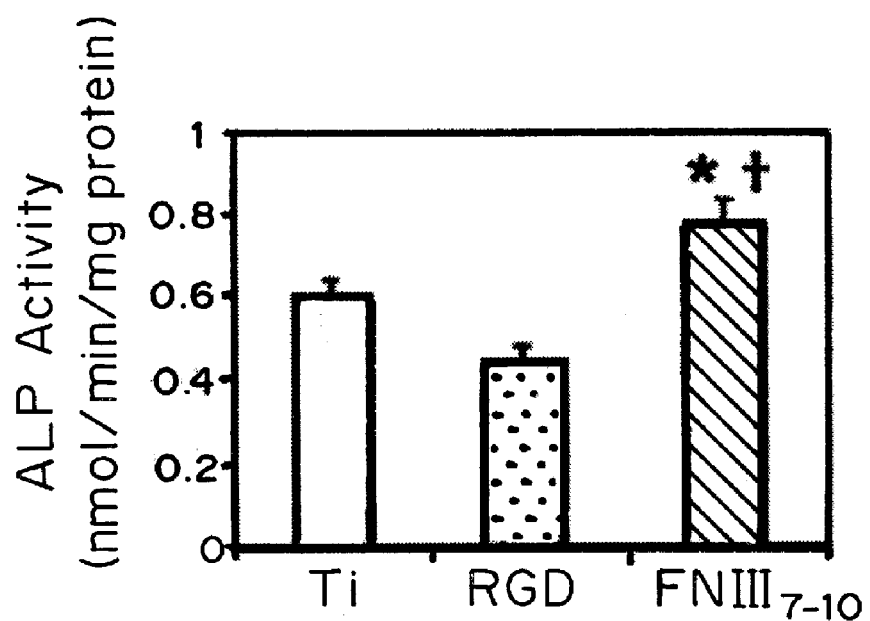
FIG. 14D is a bar graph showing alkaline phosphatase activity of cells culture on Ti, RGD-tethered or $FNIII_{7-10}$-tethered surfaces.
Figure 14E:
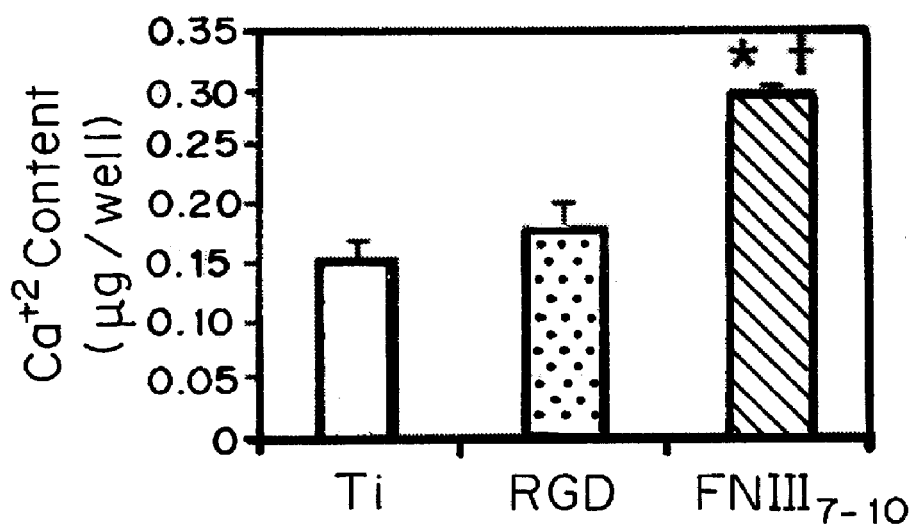
FIG. 14E is a bar graph showing calcium content in cells cultured on Ti surface, RGD-tethered surface, or $FNIII_{7-10}$-tethered surface.

Quantitative RT-PCR was used to probe osteoblastic gene expression in 7-day cultures of bone marrow stromal cells to investigate effects of integrin binding specificity on osteoblastic differentiation. Expression levels of Runx2/Cbfa1, a transcription factor essential for osteoblastic differentiation and bone formation, were elevated on the $FNIII_{7-10}$-functionalized surface compared to brushes functionalized with equimolar densities of RGD (p<0.03) (FIGS. 14A-14C). The late osteoblastic markers osteocalcin (OCN) (FIG. 14B) and bone sialoprotein (BSP) (FIG. 14C) also exhibited increased transcript levels on $FNIII_{7-10}$-tethered brushes relative to RGD functionalized supports (p<0.003). Consistent with the gene expression results, FN1 µl$_{7-10}$-tethered surfaces displayed higher alkaline phosphatase activity than RGD-functionalized surfaces (p<0.03) (FIG. 140). Finally, matrix mineralization, as determined by calcium incorporation, was used as an end-point functional marker. $FNIII_{7-10}$-engineered titanium displayed a 2-fold enhancement in mineralization relative to the ROD-tethered supports (p<0.01) (FIG. 14E). No differences were observed between ROD-functionalized brushes and serum-exposed unmodified titanium for any differentiation marker. Collectively, these results demonstrate that non-fouling brush surfaces presenting $FNIII_{7-10}$ to target $\alpha_5\beta_1$ integrin trigger enhanced osteoblastic differentiation and mineralization in primary bone marrow stromal cells compared to ROD-tethered brushes and serum-treated titanium surfaces that support $\alpha_V\beta_3$ binding.

Example 14

Assessment of Osseointegration of Engineered Surfaces

Osseointegration of implants in a rat tibia cortical bone model was quantified to evaluate the in vivo performance of the engineered titanium surfaces in bone healing. Importantly, this in vivo model provides a rigorous platform to evaluate implant coating function in a relevant orthopaedic setting. Two 2.0-mm diameter defects were drilled into the medial aspect of the proximal tibial metaphysis using a saline cooled drill. Tapered cylindrical implants (FIG. 4) of clinical-grade titanium were press-fit into the cortical defects. Implants were machined with a tapered stop collar (401) to ensure equivalent initial bone contact across all samples, and each implant had a small channel (403) spanning the head to permit subsequent pull-out testing following explanation. Biomaterial surface treatments evaluated were (i) unmodified poly(OEGMA) brushes, (ii) unmodified titanium (as a reference to the current clinical treatment), and brushes modified with either (iii) $FNIII_{7-10}$ or (iv) RGD at equimolar ligand densities (0.9 pmol/cm$^2$). In addition, a small number of implants with varying densities of $FNIII_{7-10}$ were analyzed. All implants were well-tolerated, and no complications were encountered during the course of the study. Following four weeks of implantation, the rat tibiae were harvested and analyzed for bone-implant contact by histomorphometry and implant mechanical fixation by pull-out testing.

Figure 15A:
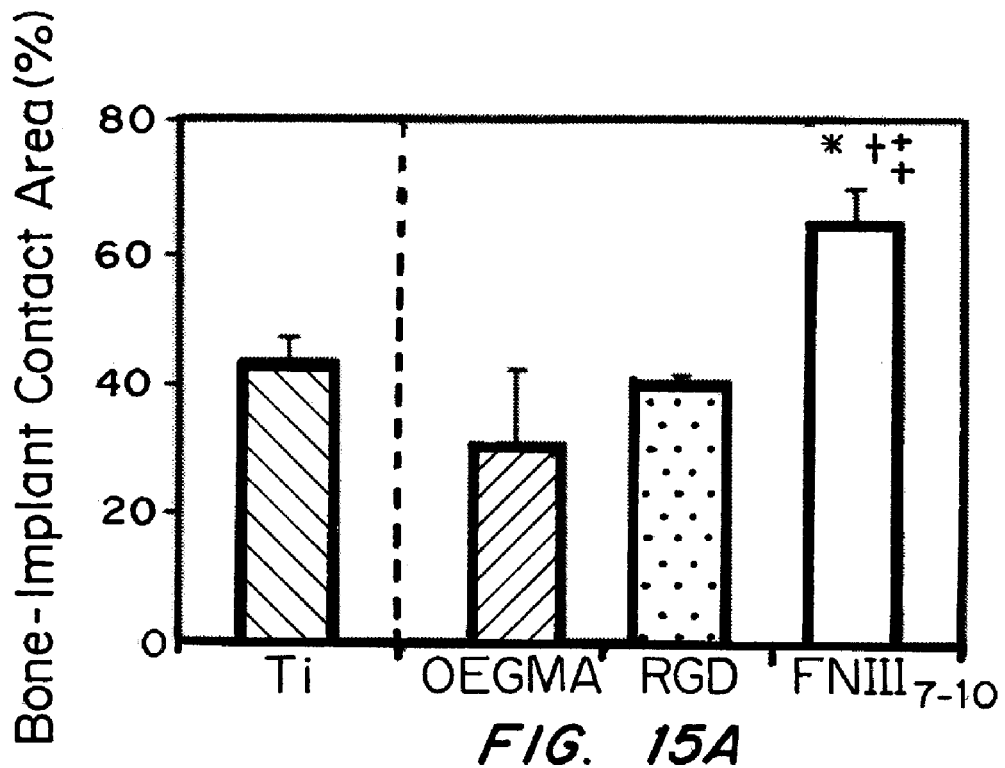
FIG. 15A is a bar graph showing percent bone-implant contact area for unmodified Ti, RGD-tethered, OEGMA-functionalized or $FNIII_{7-10}$-tethered implants.

Histological sections revealed extensive and contiguous bone matrix around $FNIII_{7-10}$-functionalized titanium implants. Less bone tissue was observed on the unmodified poly(OEGMA) brushes, poly(OEGMA) brushes with RGD tethered, and reference unmodified titanium implants, and the tissue present displayed a more porous morphology. Histomorphometric analysis of histological sections demonstrated a 70% enhancement in bone-implant contact area for $FNIII_{7-10}$-functionalized implants compared to the RGD-tethered or unfunctionalized poly(OEGMA) brushes ($p<0.02$) (FIG. 15A). Notably, the bone-implant contact area for the $FNIII_{7-10}$ group was significantly higher than that for the unmodified titanium implant ($p<0.02$). No evidence of foreign body giant cell persistence or fibrous capsule was observed in any of the sections. These findings demonstrate that controlled presentation of the integrin-specific ligand $FNIII_{7-10}$ using this polymer brush strategy significantly enhances implant integration into the host bone compared to implants presenting RGD-functionalized poly(OEGMA) brushes and the current clinical standard (unmodified titanium).

Figure 15B:
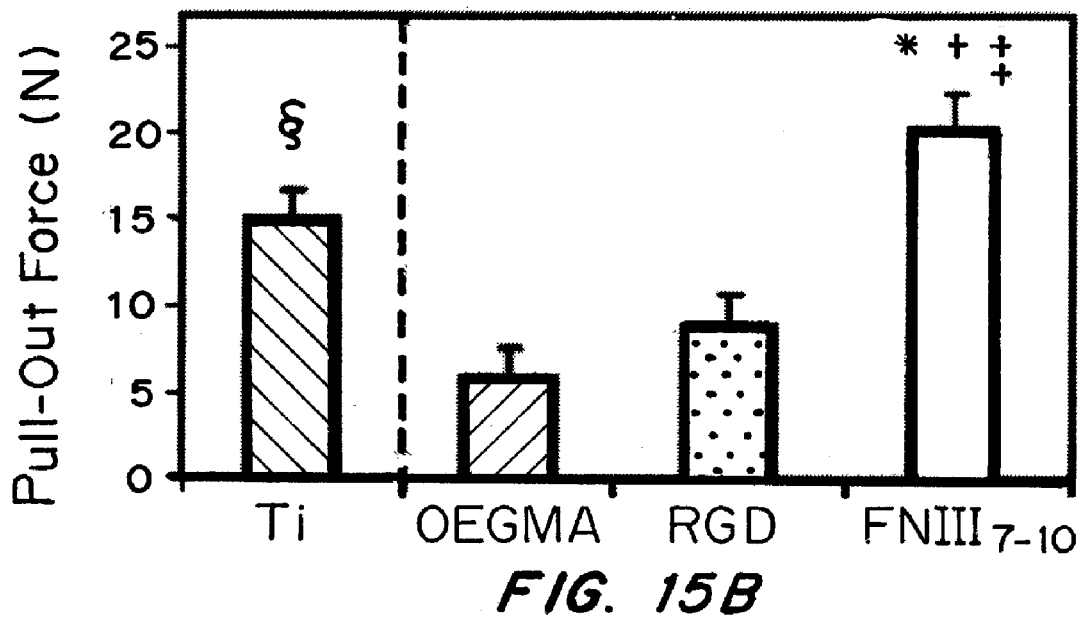
FIG. 15B is a bar graph of pull-out force (N) for unmodified Ti, RGD-tethered, OEGMA-functionalized or FNIII$_{7-10}$-tethered implants.

Mechanical fixation was used as an outcome measure of functional osseointegration. Pull-out mechanical testing revealed significantly higher mechanical fixation of the $FNIII_{7-10}$-functionalized implants over all other groups ($p<0.03$) (FIG. 15B). Implants coated with unmodified poly (OEGMA) brushes generated the lowest amount of bone apposition and mechanical fixation, suggesting that the polymer brushes retain their non-fouling/bioresistant character in vivo. $FNIII_{7-10}$-functionalized implants exhibited a 2.9-fold enhancement in fixation over RGD-tethered implants ($p<0.009$) and approximately a 4-fold improvement compared to the unmodified poly(OEGMA) brush coating ($p<0.001$). Notably, there were no differences in bone apposition or mechanical fixation between RGD-functionalized and unmodified poly(OEGMA) implants, demonstrating that presentation of the linear RGD sequence has no effects on implant osseointegration. Unmodified titanium displayed higher fixation than the unfunctionalized poly(OEGMA) brush ($p<0.01$), but the pull-out force was not statistically different from the RGD-tethered surface. Remarkably, $FNIII_{7-10}$-functionalized titanium exhibited higher mechanical fixation than the unmodified titanium ($p<0.05$), indicating that this biomolecular engineering strategy outperforms the current clinical standard.

Figure 15C:
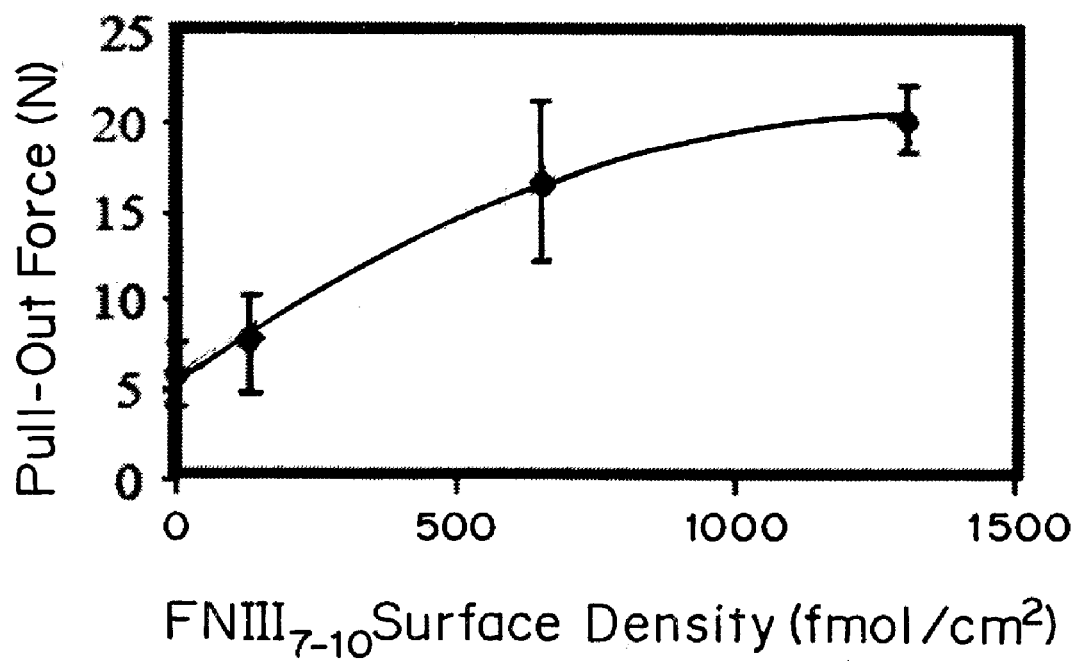
FIG. 15C is a line graph of pull-out force (N) versus FNIII$_{7-10}$ surface density (fmol/cm$^2$).

A major advantage of the poly(OEGMA) brush system described in this work is the ability to precisely control the presentation of tethered ligands. Increases in the density of tethered $FNIII_{7-10}$ yielded linearly proportional increases in available bioactive ligand in vitro. Whether the density of tethered bioadhesive ligand modulated in vivo bone healing was evaluated by implanting samples with varying tethered densities of $FNIII_{7-10}$. Mechanical fixation increased with $FNIII_{7-10}$ surface density, displaying linear increases at low surface densities and reaching a saturation limit at high densities (FIG. 15C). These results are accurately described by a simple hyperbolic relationship ($R^2=0.87$). This functional dependence is consistent with in vitro results for simple receptor-mediated phenomena such as adhesion strength. This is the first experimental study demonstrating finely tuned in vivo healing in response to engineered bioadhesive cues on material surfaces.

The data demonstrate that conferring integrin binding specificity to engineered biomaterials regulates in vitro osteoblastic differentiation of primary bone marrow stromal cells and in vivo bone healing and implant osseointegration. Importantly, this biomolecular strategy is based on surface engineering a robust non-fouling poly(OEGMA) polymer brush on clinical grade titanium, and therefore is applicable to existing biomedical implants. The integrin-specific biomaterial surfaces significantly enhanced in vivo implant integration and fixation compared to the current clinical standard (unmodified titanium) as well as biomimetic RGD-based surface treatments. The data demonstrate that in vivo host responses to implanted devices can be tailored by engineering bioadhesive ligand specificity and density. Because of the central roles of integrin receptors in numerous tissue types, this strategy of engineering integrin specificity to implanted materials may have significant impact in the rational design of biomaterials for tissue engineering and regenerative medicine.

Example 15

Use of Engineered Surfaces to Treat Bone Defects

Figure 16:
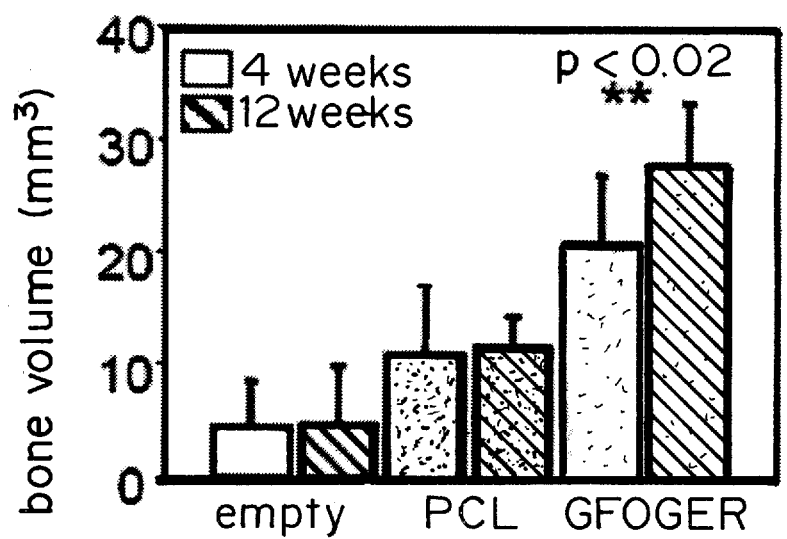
FIG. 16 is a series of bar graphs of bone volume (mm$^3$) in polycaprolactone (PCL) scaffolds and PCL scaffolds passively adsorbed with GFOGER peptide (SEQ ID NO:1) implanted in a non-healing segmental femur defect.

The ability of GFOGER peptide (SEQ ID NO:1)-coated polymeric scaffolds to heal critical sized defects was examined. Critical sized defects do not heal during the lifetime of the animal, and therefore represent rigorous models for bone repair. A 8 mm segmental defect in the rat femur was used to evaluate bone repair. Three experimental groups were evaluated: (i) empty defect controls, (ii) PCL scaffolds, and (iii) GFOGER peptide (SEQ ID NO:1)-coated PCL scaffolds. Polycaprolactone (PCL) is a clinically used polymer widely used in orthopaedic and soft tissue applications. Scaffolds were passively coated with GFOGER peptide (SEQ ID NO:1) (20 μg/ml) as described above. Bone formation was assessed non-invasively via micro-computed tomography (micro-CT) at 4 and 12 weeks. Micro-CT analysis demonstrated an enhancement in bone formation for GFOGER peptide (SEQ ID NO:1)-coated scaffolds compared to PCL and empty defects (FIG. 16). No differences in bone formation were observed between PCL and empty defects. These results demonstrate that the GFOGER peptide (SEQ ID NO:1) coating enhances bone formation in a non-healing bone defect.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A medical device comprising an integrin-specific ligand in an amount effective to increase bone tissue growth, bone tissue implantation of the device, or a combination thereof, in a subject in need thereof, wherein the integrin-specific ligand consists of $FNIII_{7-10}$ (SEQ ID NO:2).

2. The device of claim 1, wherein the device comprises metal.

3. The device of claim 2, wherein the device comprises titanium.

4. The device of claim 1, wherein the device is an implant.

5. The device of claim 1, wherein the device is an orthopaedic implant.

6. The device of claim 1, wherein the ligand is tethered to a surface of the device.

7. The device of claim 6, wherein the ligand is tethered to a polymer attached to the surface of the device.

8. The device of claim 1, wherein the device is a scaffold for bone tissue engineering.

9. A method for producing a device comprising:
adsorbing an integrin-specific ligand onto a surface of the device in an amount effective to increase bone tissue growth, bone tissue implantation of the device, or a combination thereof, in a subject in need thereof, and wherein the integrin-specific ligand consists of $FNIII_{7-10}$ (SEQ ID NO:2), wherein the device is an orthopaedic implant.

10. A method for treating a bone fracture, in a subject in need thereof, comprising implanting the device according to claim 1.

11. A method for increasing bone tissue growth, bone tissue implantation of a medical device, or a combination thereof, in a subject in need thereof, using the medical device according to claim 1, comprising increasing the surface density of integrin-specific ligand on the device, wherein increasing the surface density of the integrin-specific ligand on the device increases the bone tissue growth, bone tissue implantation of the device, or combination thereof, in a subject in need thereof, compared to devices having a lower surface density of the integrin-specific ligand.

* * * * *

SEQUENCE LISTING

```
<160> NUMBER OF SEQ ID NOS: 12

<210> SEQ ID NO 1
<211> LENGTH: 47
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (26)..(26)
<223> OTHER INFORMATION: 4Hyp

<400> SEQUENCE: 1

Gly Gly Tyr Gly Gly Gly Pro Cys Gly Pro Pro Gly Pro Pro Gly Pro
1               5                   10                  15

Pro Gly Pro Pro Gly Pro Pro Gly Phe Pro Gly Glu Arg Gly Pro Pro
            20                  25                  30

Gly Pro Pro Gly Pro Pro Gly Pro Pro Gly Pro Pro Gly Pro Cys
        35                  40                  45

<210> SEQ ID NO 2
<211> LENGTH: 368
<212> TYPE: PRT
<213> ORGANISM: artificial sequence
<220> FEATURE:
<223> OTHER INFORMATION: synthetic sequence

<400> SEQUENCE: 2

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
        35                  40                  45

Leu Glu Glu Val Val His Ala Asp Gln Ser Ser Cys Thr Phe Asp Asn
    50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro Ala Val Pro
                85                  90                  95

Pro Pro Thr Asp Leu Arg Phe Thr Asn Ile Gly Pro Asp Thr Met Arg
            100                 105                 110

Val Thr Trp Ala Pro Pro Pro Ser Ile Asp Leu Thr Asn Phe Leu Val
        115                 120                 125

Arg Tyr Ser Pro Val Lys Asn Glu Glu Asp Val Ala Glu Leu Ser Ile
    130                 135                 140

Ser Pro Ser Asp Asn Ala Val Val Leu Thr Asn Leu Leu Pro Gly Thr
145                 150                 155                 160

Glu Tyr Val Val Ser Val Ser Ser Val Tyr Glu Gln His Glu Ser Thr
                165                 170                 175
```

```
Pro Leu Arg Gly Arg Gln Lys Thr Gly Leu Asp Ser Pro Thr Gly Ile
            180                 185                 190
Asp Phe Ser Asp Ile Thr Ala Asn Ser Phe Thr Val His Trp Ile Ala
            195                 200                 205
Pro Arg Ala Thr Ile Thr Gly Tyr Arg Ile Arg His His Pro Glu His
            210                 215                 220
Phe Ser Gly Arg Pro Arg Glu Asp Arg Val Pro His Ser Arg Asn Ser
225                 230                 235                 240
Ile Thr Leu Thr Asn Leu Thr Pro Gly Thr Glu Tyr Val Val Ser Ile
            245                 250                 255
Val Ala Leu Asn Gly Arg Glu Glu Ser Pro Leu Leu Ile Gly Gln Gln
            260                 265                 270
Ser Thr Val Ser Asp Val Pro Arg Asp Leu Glu Val Val Ala Ala Thr
            275                 280                 285
Pro Thr Ser Leu Leu Ile Ser Trp Asp Ala Pro Ala Val Thr Val Arg
            290                 295                 300
Tyr Tyr Arg Ile Thr Tyr Gly Glu Thr Gly Gly Asn Ser Pro Val Gln
305                 310                 315                 320
Glu Phe Thr Val Pro Gly Ser Lys Ser Thr Ala Thr Ile Ser Gly Leu
            325                 330                 335
Lys Pro Gly Val Asp Tyr Thr Ile Thr Val Tyr Ala Val Thr Gly Arg
            340                 345                 350
Gly Asp Ser Pro Ala Ser Ser Lys Pro Ile Ser Ile Asn Tyr Arg Thr
            355                 360                 365

<210> SEQ ID NO 3
<211> LENGTH: 7
<212> TYPE: PRT
<213> ORGANISM: artificial sequence
<220> FEATURE:
<223> OTHER INFORMATION: synthetic peptide

<400> SEQUENCE: 3

Gly Arg Gly Asp Ser Pro Cys
1               5

<210> SEQ ID NO 4
<211> LENGTH: 22
<212> TYPE: PRT
<213> ORGANISM: artificial sequence
<220> FEATURE:
<223> OTHER INFORMATION: synthetic sequence

<400> SEQUENCE: 4

Gly Arg Gly Asp Gly Gly Gly Gly Gly Gly Gly Gly Gly Gly Gly Gly
1               5                   10                  15

Gly Pro His Ser Arg Asn
            20

<210> SEQ ID NO 5
<211> LENGTH: 20
<212> TYPE: DNA
<213> ORGANISM: artificial sequence
<220> FEATURE:
<223> OTHER INFORMATION: synthetic primer

<400> SEQUENCE: 5
ggccttcaag gttgtagccc                                              20

<210> SEQ ID NO 6
```

```
<211> LENGTH: 16
<212> TYPE: DNA
<213> ORGANISM: artificial sequence
<220> FEATURE:
<223> OTHER INFORMATION: synthetic primer

<400> SEQUENCE: 6
cccggccatg acggta                                                        16

<210> SEQ ID NO 7
<211> LENGTH: 20
<212> TYPE: DNA
<213> ORGANISM: artificial sequence
<220> FEATURE:
<223> OTHER INFORMATION: synthetic primer

<400> SEQUENCE: 7
acgagctagc ggaccacatt                                                    20

<210> SEQ ID NO 8
<211> LENGTH: 20
<212> TYPE: DNA
<213> ORGANISM: artificial sequence
<220> FEATURE:
<223> OTHER INFORMATION: synthetic primer

<400> SEQUENCE: 8
ccctaaacgg tggtgccata                                                    20

<210> SEQ ID NO 9
<211> LENGTH: 21
<212> TYPE: DNA
<213> ORGANISM: artificial sequence
<220> FEATURE:
<223> OTHER INFORMATION: synthetic primer

<400> SEQUENCE: 9
tgacgctgga aagttggagt t                                                  21

<210> SEQ ID NO 10
<211> LENGTH: 19
<212> TYPE: DNA
<213> ORGANISM: artificial sequence
<220> FEATURE:
<223> OTHER INFORMATION: synthetic primer

<400> SEQUENCE: 10
gccttgccct ctgcatgtc                                                     19

<210> SEQ ID NO 11
<211> LENGTH: 5
<212> TYPE: PRT
<213> ORGANISM: Artificial Sequence
<220> FEATURE:
<223> OTHER INFORMATION: Synthetic construct

<400> SEQUENCE: 11

Pro His Ser Arg Asn
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
```

```
<222> LOCATION: (3)..(3)
<223> OTHER INFORMATION: 4Hyp

<400> SEQUENCE: 12

Gly Phe Pro Gly Glu Arg
1               5
```